United States Patent [19]

Geach et al.

[11] Patent Number: 5,489,570
[45] Date of Patent: Feb. 6, 1996

[54] HERBICIDAL ISOXAZOLES

[75] Inventors: Neil Geach; David W. Hawkins; Christopher J. Pearson; Philip H. G. Smith; Nicolas White, all of Ongar, England

[73] Assignee: Rhone-Poulenc Agriculture Limited, Essex, England

[21] Appl. No.: 282,546

[22] Filed: Jul. 29, 1994

[30] Foreign Application Priority Data

Jul. 30, 1993 [GB] United Kingdom .................... 9315796
Mar. 17, 1994 [GB] United Kingdom .................... 9405223

[51] Int. Cl.$^6$ ................... A01N 43/828; A01N 43/80; C07D 285/06; C07D 261/08
[52] U.S. Cl. ................... 504/261; 504/270; 504/271; 548/248; 548/217; 548/127
[58] Field of Search .................................. 548/248, 217, 548/127, 248; 504/271, 261, 270

[56] References Cited

U.S. PATENT DOCUMENTS

| | | | |
|---|---|---|---|
| 3,852,298 | 12/1974 | Wagner et al. | 260/304 |
| 4,414,214 | 11/1983 | Habicht et al. | 424/248.51 |
| 4,740,519 | 4/1988 | Shroot et al. | 514/443 |
| 4,794,188 | 12/1988 | Musser et al. | 546/152 |
| 5,001,124 | 3/1991 | Patterson et al. | 514/236.8 |
| 5,244,893 | 9/1993 | Elbe et al. | 514/212 |
| 5,371,099 | 12/1994 | Bartlett et al. | 514/378 |

FOREIGN PATENT DOCUMENTS

| | | |
|---|---|---|
| 0418175 | 3/1991 | European Pat. Off. . |
| 0487357 | 5/1992 | European Pat. Off. . |
| 0527036 | 2/1993 | European Pat. Off. . |
| 0527037 | 2/1993 | European Pat. Off. . |
| 0588357 | 3/1994 | European Pat. Off. . |

OTHER PUBLICATIONS

Shimizu, T.; Hayashi, Y.; and Teramura, K.; Bull. Chem. Soc. Jpn. 58, 2519–2522 (1985). Sep.
Kim, J. Y.; and Ryu, E. K.; Heterocycles vol. 31 No. 9 1693–1697 (1990).

*Primary Examiner*—Johann Richter
*Assistant Examiner*—Laura L. Stockton
*Attorney, Agent, or Firm*—Burns, Doane, Swecker & Mathis

[57] ABSTRACT

The invention relates to isoxazole derivatives of formula (I):

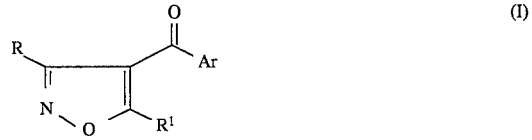

wherein:

Ar represents phenyl optionally substituted by from one to three groups and wherein two substituents on adjacent positions of the phenyl ring, together with the two atoms to which they are attached, form a 5- to 7-membered ring which is optionally substituted;

R represents the hydrogen atom or a group —$CO_2R^3$;

$R^1$ represents alkyl, haloalkyl or optionally substituted cycloalkyl;

$R^3$ represents alkyl, alkenyl or alkynyl containing up to six carbon atoms which is optionally substituted by one or more halogen atoms;

and their use as herbicides.

36 Claims, No Drawings

HERBICIDAL ISOXAZOLES

This invention relates to novel isoxazole derivatives, compositions containing them, processes for their preparation and their use as herbicides.

The present invention provides isoxazoles of formula I:

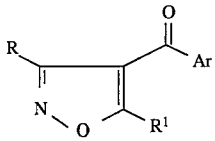

wherein:
Ar represents phenyl optionally substituted by from one to three groups $R^2$ which may be the same or different and wherein two substituents on adjacent positions of the phenyl ring. together with the two atoms to which they are attached, form a 5- to 7-membered ring which is optionally substituted by one or more groups $R^{21}$ which may be the same or different;

R represents the hydrogen atom or a group —$CO_2R^3$;

$R^1$ represents:
  a straight- or branched-chain alkyl group containing from one to six carbon atoms which is optionally substituted by one or more halogen atoms; or
  a cycloalkyl group containing from three to six carbon atoms optionally substituted by one or more groups selected from $R^4$, —$CO_2R^4$, —$SR^4$, halogen and —$OR^4$;

$R^2$ represents:
  a halogen atom,
  a straight- or branched-chain alkyl group containing from one to six carbon atoms which is substituted by a group —$OR^4$;
  a group selected from $R^4$, —$CO_2R^4$, —$COR^4$, —$SR^5$, —$SOR^5$, —$SO_2R^5$, —$OSO_2R^5$, —$OR^5$, —$O(CH_2)m$—$OR^4$, —$NR^6R^7$, —$N(R^8)SO_2R^5$, —$(CR^9R^{10})_t$—$S(O)_pR^5$, nitro, cyano and —$NR^{11}R^{12}$;

$R^{21}$ is as hereinbefore defined for $R^2$ or represents =O, =S, cyclic ketal or cyclic thioketal;

$R^3$ and $R^4$, which may be the same or different, each represent a straight- or branched-chain alkyl, alkenyl or alkynyl group containing up to six carbon atoms which is optionally substituted by one or more halogen atoms;

$R^5$ represents a group $R^4$, or phenyl optionally substituted by from one to five groups which may be the same or different selected from halogen, $R^4$, —$CO_2R^4$, —$COR^4$, —$OR^4$, nitro, cyano and —$O(CH_2)_m$—$OR^4$;

$R^6$ and $R^7$, which may be the same or different, each represent the hydrogen atom or a straight- or branched-chain alkyl group containing from one to six carbon atoms which is optionally substituted by one or more halogen atoms;

m represents an integer from one to three;

$R^8$ represents the hydrogen atom; a straight- or branched-chain alkyl, alkenyl or alkynyl group containing up to six carbon atoms optionally substituted by one or more halogen atoms; a cycloalkyl group containing from three to six carbon atoms; or phenyl optionally substituted by from one to five groups $R^2$ which may be the same or different;

$R^9$ and $R^{10}$, which may be the same or different, each represents:
  the hydrogen atom; a straight- or branched-chain, alkyl group containing up to 6 carbon atoms which is optionally substituted by one or more halogen atoms; or phenyl optionally substituted by from one to five groups which may be the same or different selected from halogen, $R^4$, —$CO^2R^4$, —$COR^4$, —$OR^4$, nitro, cyano and —$O(CH_2)_m$—$OR^4$;

$R^{11}$ represents —$COR^4$ or —$CO_2R^4$;

$R^{12}$ represents:
  the hydrogen atom;
  a straight- or branched-chain alkyl group containing up to six carbon atoms optionally substituted by one or more halogen atoms;
  or a cycloalkyl group containing from three to six carbon atoms;

p is zero, one or two;

t represents an integer from one to three; where t is greater than one the groups —$CR^9R^{10}$— may be the same or different;

and agriculturally acceptable salts thereof, which possess valuable herbicidal properties.

In certain cases the substituents R, $R^1$, $R^2$, $R^3$, $R^4$, $R^5$, $R^6$, $R^7$, $R^8$, $R^9$, $R^{10}$ and $R^{21}$ contribute to optical isomerism and/or stereo isomerism. All such forms are embraced by the present invention.

The 5- to 7-membered ring forming part of the group Ar is carbocyclic or heterocyclic containing one or more heteroatoms, preferably selected from oxygen, sulphur and nitrogen (preferably from one to four), it being understood that a sulphur atom, where present, may be in the form of a group —SO— or —$SO_2$-, and may be aromatic, saturated or partially saturated.

Where $R^{21}$ represents cyclic ketal or cyclic thioketal preferably the ketal or thioketal ring contains 5 or 6 ring members.

Examples of the group Ar include the following optionally substituted ring systems and corresponding dihydro compounds (where applicable):

benzo-1,2,3-thiadiazole, benzo[b]thiophene, benzo[b]furan, benzo[c]thiophene, benzo[c]furan, benzthiazole, 1,2-benzisothiazole, 2,1-benzisothiazole, 1,2-benzthiazin, 2,1-benzthiazin, 1,3-benzothiazine, 1,4-benzothiazine, benzimidazole, indazole, thiochroman, chroman, 2H-thiochromene, 2H-chromene, 4H-thiochromene, 4H-chromene, isothiochroman, isochroman, isothiochromene, isochromene, benzofurazan 1,3-benzodithiole, 1,3-benzodioxole, 1,3-benzoxathiole, 1,4-benzodithiin, 1,4-benzoxathiin, 1,3-benzoxathian, 3,1-benzoxathian, 1,3-benzodithian, benzoxazole and 1,3-benzoxazol-2-one, indole, isoindole, 1,4-benzodioxin, 1,3-benzodioxin.

By the term "agriculturally acceptable salts" is meant salts the cations of which are known and accepted in the an for the formation of salts for agricultural or horticultural use. Preferably the salts are water-soluble.

Suitable acid addition salts formed by compounds of formula I include salts with inorganic acids, for example hydrochlorides, sulphates, phosphates and nitrates and salts with organic acids, for example acetic acid.

Compounds of formula I in which Ar represents optionally substituted 1,3-benzodioxole, benzo[b]thiophene, benzoxazole or benzo-1,2,3-thiadiazole are preferred.

A further preferred class of compounds of formula I are those wherein:
(a) $R^2$ is located at C-2 of the phenyl ring when fusion is at C-3 and C-4 of that ring, and
(b) $R^2$ is located at C-4 of the phenyl ring when fusion is at C-2 and C-3 of that ring.

Preferably $R^2$ represents a halogen atom or a group selected from —$SR^5$, —$SOR^5$, —$SO_2R^5$, $R^4$ and —$OR^5$.

Preferably $R^{21}$ represents a halogen atom (e.g. fluorine), $C_{1-4}$ alkyl (e.g. butyl) or —$OR^5$ (e.g. methoxy).

Preferably R 1 represents a straight- or branched-chain alkyl group containing up to four carbon atoms; or a cyclopropyl group optionally substituted by a group $R^4$.

Compounds of formula (I) in which R represents hydrogen are also preferred.

A further preferred class of compounds of formula (I) are those wherein:

Ar represents phenyl optionally substituted by a group $R^2$ and wherein two substituents on adjacent positions of the phenyl ring, together with the two atoms to which they are attached, form a 5- or 6-membered ring selected from dioxolane, thiophene, thiophene-S,S-dioxide, thiadiazole, oxazole, pyrrole and dioxane, which ring is optionally substituted by one or two groups $R^{21}$ which may be the same or different;

R represents the hydrogen atom;

$R^1$ represents a cyclopropyl group;

$R^2$ represents:
a halogen atom or a group selected from —$SR^5$, —$SOR^5$, —$SO^2R^5$, —$CH_2S(O)_pR^5$, $R^4$ and —$OR^5$;

$R^{21}$ represents a halogen atom (e.g. fluorine), $C_{1-4}$ alkyl, —$SO_2R^5$ or —$OR^5$;

$R^4$ represents methyl;

$R^5$ represents methyl or ethyl; and p is zero, one or two (preferably two).

Particularly important compounds include the following:
1. 5-cyclopropyl-4-(2,2-difluoro-7-methylsulphenyl-1,3-benzodioxol-4-oyl)isoxazole;
2. 5-cyclopropyl-4-(2,2-difluoro-1,3-benzodioxol-4-oyl)isoxazole;
3. 5-cyclopropyl-4-(3,4-dimethoxybenzo[b]thien-5-oyl)isoxazole;
4. 5-cyclopropyl-4-(benzo-1,2,3-thiadiazol-5-oyl)isoxazole;
5. 5-cyclopropyl-4-(2,2-difluoro-7-methylsulphonyl-1,3-benzodioxol-4-oyl)isoxazole;
6. 5-cyclopropyl-4-(2,2-difluoro-4-methylsulphonyl-1,3-benzodioxol-5-oyl)isoxazole;
7. 4-(2-t-butyl-4-chlorobenzoxazol-7-oyl)-5-cyclopropylisoxazole;
8. 4-(4-chloro-3-methoxybenzo[b]thien-5-oyl)-5-cyclopropylisoxazole;
9. 5-cyclopropyl-4-(2,2-difluoro-4-methylsulphinyl-1,3-benzodioxol-5-oyl)isoxazole;
10. 5-cyclopropyl-4-(2,2-difluoro-4-methylsulphenyl-1,3-benzodioxol-5-oyl)isoxazole;
11. 5-cyclopropyl-4-[1-(methylsulphonyl)indole-4-carbonyl]isoxazole;
12. 5-cyclopropyl-4-(4-methyl-1,3-benzodioxol-5-oyl)isoxazole;
13. 5-cyclopropyl-4-[4-(methanesulphonylmethyl)-1,3-benzodioxol-5-oyl]isoxazole;
14. 5-cyclopropyl-4-[2,2-difluoro-4-(methanesulphonylmethyl)-1,3-benzodioxol-5-oyl]isoxazole;
15. 5-cyclopropyl-4-[4-(methylsulphenyl)-1,3-benzodioxol-5-oyl]isoxazole;
16. 5-cyclopropyl-4-[3-ethoxy-4-(methylsulphenyl)benzo[b]thien-5-oyl]isoxazole;
17. 5-cyclopropyl-4-(4-chloro-3-ethoxy-2-ethylbenzo[b]thien-5-oyl)isoxazole;
18. 5-cyclopropyl-4-(4-chloro-3-ethoxybenzo[b]thien-5-oyl)isoxazole;
19. 5-cyclopropyl-4-[5-(methylsulphonyl)-1,4-benzodioxan-6-carbonyl]isoxazole;
20. 5-cyclopropyl-4-[4-(methylsulphonyl)-1,3-benzodioxol-5-oyl]isoxazole;
21. 5-cyclopropyl-4-[5-(methylsulphinyl)-1,4-benzodioxan-6-carbonyl]isoxazole;
22. 5-cyclopropyl-4-[4-(methylsulphinyl)-1,3-benzodioxol-5-oyl]isoxazole;
23. 5-cyclopropyl-4-(4-chloro-3-methoxybenzo[b]thien-5-oyl)isoxazole-1,1-dioxide;
24. 5-cyclopropyl-4-(3,4-dimethoxybenzo[b]thien-5-oyl)isoxazole-1,1-dioxide;
25. 5-cyclopropyl-4-(4-chloro-3-methoxy-2-methylbenzo[b]thien-5-oyl)isoxazole-1,1-dioxide;
26. 5-cyclopropyl-4-[5-(methylsulphenyl)-1,4-benzodioxan-6-carbonyl]isoxazole; and
27. 5-cyclopropyl-4-(4-chloro-3-methoxy-2-methylbenzo[b]thien-5-oyl)isoxazole.

The numbers 1 to 27 are assigned to these compounds for reference and identification hereinafter.

Compounds of formula I may be prepared by the application or adaptation of known methods (i.e. methods heretofore used or described in the literature), for example as hereinafter described.

It is to be understood that in the descriptions of the following processes the sequences may be performed in different orders, and that suitable protecting groups may be required to achieve the compounds sought.

According to a feature of the present invention compounds of formula I in which R represents hydrogen may be prepared by the reaction of a compound of formula (II):

wherein Ar and $R^1$ are as hereinbefore defined and L is a leaving group, with a salt of hydroxylamine. Hydroxylamine hydrochloride is generally preferred. Generally L is alkoxy, for example ethoxy, or N,N-dialkylamino, for example N,N-dimethylamino. The reaction is generally carried out in a solvent such as ethanol or acetonitrile, optionally in the presence of a base or acid acceptor such as triethylamine or sodium acetate.

According to a further feature of the present invention compounds of formula I in which R represents hydrogen may be prepared by the reaction of a compound of formula (III):

wherein $R^1$ is as hereinbefore described and Y represents a carboxy group or a reactive derivative thereof (such as a carboxylic acid chloride or carboxylic ester), or a cyano group, with an organometallic reagent of formula (IV):

wherein Ar is as hereinbefore defined and M represents an alkali metal, a metal bonded to one or more ligands, or a Grignard group. Preferably M represents lithium, or a magnesium-containing Grignard group. The reaction is generally carried out in an inert solvent such as diethyl ether or tetrahydrofuran at a temperature from −78° C. to the reflux temperature of the mixture.

According to a further feature of the present invention compounds of formula I wherein R represents a group —CO$_2$R$^3$ may be prepared by the reaction of a compound of formula (V):

ArCOCH=C(P)R$^1$  (V)

wherein Ar and R$^1$ are as hereinbefore defined and P is a leaving group, with a compound of formula R$^3$O$_2$CC(X)=NOH wherein R$^3$ is as hereinbefore defined and X is a halogen atom. Generally X is chlorine or bromine and P represents N,N-dialkylamino. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula I in which R represents a group —CO$_2$R$^3$ may be prepared by the reaction of a compound of formula (VI):

ArCOC≡CR$^1$  (VI)

wherein Ar and R$^1$ are as hereinbefore defined, with a compound of formula R$^3$O$_2$CC(X)=NOH wherein R$^3$ and X are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula I wherein R represents —CO$_2$R$^3$ may be prepared by the reaction of the salt of a compound of formula (VII):

ArCOCH$_2$COR$^1$  (VII)

wherein Ar and R$^1$ are as hereinbefore defined, with a compound of formula R$^3$O$_2$CC(X)=NOH wherein R$^3$ and X are as hereinbefore defined. Preferred salts include sodium or magnesium salts. The reaction may be performed in an inert solvent such as dichloromethane or acetonitrile at a temperature between room temperature and the reflux temperature of the mixture.

According to a further feature of the present invention compounds of formula I in which R represents hydrogen may be prepared by the reaction of a compound of formula (VIII):

(VIII)

wherein R 1 is as hereinbefore defined with a compound of formula Ar—H, wherein Ar is as hereinbefore defined, The reaction is generally performed in the presence of a Lewis acid catalyst such as aluminium trichloride, in an inert solvent at a temperature from 0° C. to the reflux temperature of the mixture.

Intermediates in the preparation of compounds of formula I may be prepared by the application or adaptation of known methods, for example as described hereinafter.

Compounds of formula (II) in which L represents O-alkyl or N,N-dialkylamino may be prepared by the reaction of the corresponding compound of formula (VII) with either a trialkyl orthoformate such as triethyl orthoformate or a dimethylformamide dialkylacetal such as N,N-dimethylformamide dimethyl acetal. The reaction with triethyl orthoformate is generally carried out in the presence of acetic anhydride at the reflux temperature of the mixture and the reaction with N,N-dimethyl formamide dialkyl acetal is carried out optionally in the presence of an inert solvent at a temperature from room temperature to the reflux temperature of the mixture.

Compounds of formula (V) may be prepared by the reaction of a compound of formula (IX):

R$^1$(P)C=CH$_2$  (IX)

wherein R$^1$ and P are as hereinbefore defined, with an acid chloride of formula (X):

ArCOCl  (X)

wherein Ar is as hereinbefore defined. The reaction is generally carried out in the presence of an organic base such as triethylamine in an inert solvent such as toluene or dichloromethane at a temperature between −20° C. and room temperature.

Compounds of formula (VI) may be prepared by the metallation of the appropriate acetylene of formula (XI):

R$^1$—C≡CH  (XI)

wherein R$^1$ is as hereinbefore defined, followed by reaction of the metal salt thus obtained with an acid chloride of formula (X). The metallation is generally performed using n-butyl lithium in an inert solvent such as ether or tetrahydrofuran at a temperature from −78° C. to 0° C. The subsequent reaction with the acid chloride is carried out in the same solvent at a temperature between −78° C. and room temperature.

Compounds of formula (VII) may be prepared by the reaction of an ester of formula (XII):

Ar—CO$_2$Z  (XII)

wherein Ar is as hereinbefore defined and Z is an alkyl group, with a ketone of formula R$^1$C(O)CH$_3$, wherein R$^1$ is as hereinbefore defined, in the presence of a base. Generally the base used is sodium hydride and the reaction is performed in an inert solvent at a temperature from 0° C. to reflux.

Compounds of formula (VII) may also be prepared by the reaction of a compound of formula (XIII):

Ar—COCH$_3$  (XIII)

wherein Ar and is as hereinbefore defined, with an ester of formula R$^1$CO$_2$Z, wherein R$^1$ and Z are as hereinbefore defined, in the presence of a base. Preferably Z represents a methyl, ethyl or t-butyl group. Generally the base used is sodium hydride and the reaction is performed in an inert solvent at a temperature from 0° C. to reflux.

Compounds of formula (VII) may also be prepared by the reaction of an acid chloride of formula (X) with the metal salt of a compound of formula (XIV):

R$^1$COCH$_2$CO$_2$tBu  (XIV)

wherein R$^1$ is as hereinbefore defined, to give a compound of formula (XV):

ArCOCH(COR¹)CO₂tB  (XV)

wherein Ar and R¹ is as hereinbefore defined, which is decarboxylated to give a compound of formula (VII). Generally the reaction to produce the compound of formula (XIV) is performed in a solvent such as a lower alcohol, preferably methanol, in the presence of a metal, preferably magnesium. The decarboxylation is generally performed by refluxing the compound of formula (XV) in the presence of a catalyst, such as para-toluenesulphonic acid, in an inert solvent e.g. toluene.

Compounds of formula (XIII) are known or may be prepared by the application or adaptation of -known methods. For example, compounds of formula (XIII) in which Ar represents an optionally substituted 1,2,3-benzthiadiazole may be prepared by the diazotisation and subsequent cyclisation of an amine of formula (XVI):

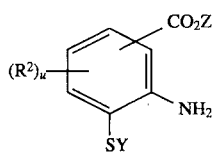

(XVI)

wherein R² and Z are as hereinbefore defined, u is zero or an integer from one to three and Y represents hydrogen or a group which may be cleaved during cyclisation. Preferably Y is hydrogen or benzyl. The reaction is preferably carried out using an aqueous solution of sodium nitrite in the presence of a strong acid, preferably hydrobromic acid, at a temperature from 0° to 20° C.

Intermediates of formula (III), (IV), (VIII), (IX), (X), (XI), (XII), (XIV) and (XVI) are known or may be prepared by the application or adaptation of known methods.

Those skilled in the an will appreciate that some compounds of formula I may be prepared by the interconversion of other compounds of formula I and such interconversions constitute yet more features of the present invention. Examples of such interconversions are hereafter described.

According to a further feature of the present invention compounds in which R² and/or R²¹ is —SOR⁵, —SO₂R⁵, —(CR⁹R¹⁰)ᵣ—SOR⁵ or —(CR⁹R¹⁰)ᵣ—SO₂R⁵ may be prepared by the oxidation of the sulphur atom of the corresponding compound in which R² and/or R²¹ is —SR⁵, —SOR⁵, —(CR⁹R¹⁰)ᵣ—SR⁵ or —(CR⁹R¹⁰)ᵣ—SOR⁵. According to a further feature of the present invention compounds of formula (I) in which Ar includes a sulphur atom in the 5- to 7-membered ring in the form of a group —SO— or —SO₂— may be prepared by the oxidation of the corresponding compound of formula (I) in which the ring contains an unoxidised sulphur atom. In both of the above cases the oxidation of the sulphur atom is generally carried out using for example 3-chloroperoxybenzoic acid in an inert solvent such as dichloromethane at a temperature from –40° C. to room temperature.

According to a further feature of the present invention compounds in which R² and/or R²¹ represents —(CR⁹R¹⁰)ᵣ—S(O)ₚR⁵ wherein R⁵ and p are as hereinbefore defined may be prepared by reacting the corresponding compound in which R² and/or R²¹ is replaced by —(CR⁹R¹⁰)ᵣ—L¹, wherein L¹ is halogen (preferably bromine), with a compound of formula HS(O)ₚR⁵ wherein R⁵ and p are as hereinbefore defined. The reaction is generally performed in a solvent such as tetrahydrofuran or ethanol, optionally in the presence of a base such as sodium hydride or sodium alkoxide (e.g. sodium ethoxide), and at a temperature from 0° C. to the reflux temperature of the solvent.

Compounds in which R² and/or R²¹ represents —(CR⁹R¹⁰)ᵣ-L¹ wherein t is one may be prepared by reacting the corresponding compound in which R² and/or R²¹ is replaced by —(CR⁹R¹⁰)ᵣ—H with a halogenating agent, such as an N-halosuccinimide (e.g. N-bromosuccinimide). Where the halogenating agent is an N-halosuccinimide the reaction is generally performed in an inert solvent such as-carbon tetrachloride or dichloromethane under irradiation with ultraviolet or tungsten light, at a temperature from room temperature to the reflux temperature of the solvent.

Compounds of formula (I) may be convened into agriculturally acceptable salts thereof by known methods or by the application and adaptation of known methods.

The following Examples illustrate the preparation of compounds of formula I and the following Reference Examples illustrate the preparation of intermediates of the invention. In the present specification b.p. means boiling point; m.p. means melting point. Where the letters NMR appear, mere follow the characteristics of a proton nuclear magnetic spectrum.

EXAMPLE 1

A solution of 4-(3-cyclopropyl-2-dimethylaminomethylene-1,3 -dioxopropyl)-2,2-difluoro-7-methylsulphenyl-1,3-benzodioxole (6.24 g) and hydroxylamine hydrochloride (1.39 g) was stirred overnight in ethanol. After cooling to –15° C. the precipitated solid was filtered off and washed with cold ethanol. The filtrate was evaporated and chromatographed on silica gel eluting with ethyl acetate/cyclohexane to give 5-cyclopropyl-4-(2,2-difluoro-7 -methylsulphenyl-1,3-benzodioxo-4-oyl)isoxazole (compound 1, 0.86 g), m.p. 97°–98° C.

By proceeding in a similar manner the following compounds were prepared:

5-cyclopropyl-4-(2,2-difluoro-1,3-benzodioxol-4-oyl) isoxazole (compound 2) as a gum, NMR (CDCl₃) δ1.3 (2H,m), 1.4 (2H,m), 2.8 (1H,m) 7.25 (2H,m), 7.45 (1H,m), 8.35 (1H,s).

5-cyclopropyl-4-[1-(methylsulphonyl)indole-4-carbonyl] isoxazole (compound 11) as a green solid, m.p. 142°–144° C.

5-cyclopropyl-4-(4-methyl-1,3-benzodioxol-5-oyl)isoxazole (compound 12) as a white solid, m.p. 124°–126° C.

5-cyclopropyl-4-[4-(methylsulphonylmethyl)-1,3-benzodioxol-5 -oyl]isoxazole (compound 13) as a beige solid, m.p. 206°–20820 C.

5-cyclopropyl-4-[2,2-difluoro-4-(methylsulphonylmethyl)-1,3 -benzodioxol-5-oyl]isoxazole (compound 14) as a yellow solid, m.p. 180°–181° C.

5-cyclopropyl-4-[4-(methylsulphenyl)-1,3-benzodioxol-5-oyl]isoxazol (compound 15) as a yellow gum, NMR (CDCl₃) δ 1.2(2H,m), 1.3(2H,m), 2.4(3H,s), 2.7(1H, m), 6.1(2H,s), 6.8(1H,d), 7.0(1H,d), 8.2(1H,s).

5-cyclopropyl-4-[5-(methylsulphenyl)-1,4-benzodioxan-6-carbonyl]isoxazole (compound 26) as a cream solid, m.p. 135°–136° C.

EXAMPLE 2

A solution containing 5-(3-cyclopropyl-2-ethoxymethylene-1,3 -dioxoprop-1-yl)-3,4-dimethoxybenzo[b]thiophene (0.59 g) and hydroxylamine hydrochloride (0.137 g) was stirred for 15 minutes in ethanol. Sodium acetate (anhydrous, 0.161 g) was added and the mixture stirred for 4 hours, before evaporation of the ethanol and addition of water. The mixture was extracted with ethyl acetate, dried (anhydrous magnesium sulphate) and evaporated in vacuo. The residue was purified by column chromatography on silica, eluting with ether/cyclohexane to yield 5-cyclopropyl-4-(3,4dimethoxybenzo[b]thien-5-oyl)isoxazole (compound 3, 0.24 g) as an oil, NMR $\delta$1.20 (2H,m), 1.35 (2H,m), 2.80 (1H,m), 3.84 (3H,s), 4.00 (3H,s), 6.39 (1H,s), 7.40 (1H, d), 7.59 (1H, d), 8.29 (1H,s).

By proceeding in a similar manner the following compounds were prepared:

5-cyclopropyl-4-(benzo-1,2,3-thiadiazol-5-oyl)isoxazole (compound 4) as a pale yellow oil, NMR (CDCl$_3$) $\delta$1.23 (2H,m), 1.34(2H,m), 2.70(1H,m), 8.07 (1H, dd), 8.17 (1H, d), 8.40 (1H,s), 8.96 (1H, d).

5-cyclopropyl-4-[3-ethoxy-4-(methylsulphenyl)benzo[b]thien-5-oyl]isoxazole (compound 16) as an orange gum NMR (CDCl$_3$) $\delta$ 1.1(2H,m), 1.3(2H,m), 1.5(3H,t), 2.4(3H,s), 2.5(1H,m), 4.1(2H,q), 6.4(1H,s), 7.21H,d), 7.7(1H,d), 8.1(1H,s).

5-cyclopropyl]-4-(4-choro-3-ethoxy-2-ethylbenzo[b]thien-5 -oxy)isoxazole (compound 17) obtained as an orange gum, NMR (CDCl$_3$) $\delta$1.1(2H,m), 1.3(5H,m), 1.4(3H,t) 2.6(1H,m), 2.9(2H,q), 3.9(2H,q), 7.1(1H,d), 7.6(1H,d), 8.1(1H,s).

5-cycopropyl-4-(4-choro3-ethoxybenzo[b]thien-5-oyl-)isoxazole (compound 18) obtained as a brown gum, NMR (CDCl$_3$) $\delta$1.2(2H,m), 1.4(2H,m), 1.5(3H,t), 2.7(1H,m), 4.2(2H,q), 65(1H,s), 7.3(1H,d), 7.7(1H,d), 8.2(1H,s).

5-cyclopropyl-4-(4-chloro-3-methoxy-2-methylbenzo[b]thien-5-oyl)isoxazole (compound 27) as a yellow gum, NMR (CDCl$_3$) $\delta$1.2(2H,m), 1.4(2H,m), 2.5(3H,s), 2.6(1H,m), 3.9(3H,s), 7.3(1H,d), 7.7(1H,d), 8.2(1H,s).

EXAMPLE 3

A solution of 5-cyclopropyl-4-(2,2-difluoro-7-methylsulphenyl-1,3 -benzodioxol-4-oyl)isoxazole (0.64 g) in dichloromethane was treated with m-chloroperbenzoic acid (55%, 1.5 g). After 2 hours the mixture was cooled to 1° C., and 1M sodium metabisulphite solution added. The filtered solution was separated and the organic phase washed with sodium acetate solution, brine, dried over anhydrous sodium sulphate and evaporated to give 5-cyclopropyl-4-(2,2 -difluoro-7-methylsulphonyl-1,3-benzodioxol-4-oyl)isoxazole (compound 5, 0.35 g) as a white solid, m.p. 164°–165° C.

By proceeding in a similar manner the following compounds were prepared:

5-cyclopropyl-4-[5-(methylsulphonyl)-1,4-benzodioxan-6-carbonyl]isoxazole (compound 19) as a cream solid, m.p. 174°–175° C.

5-cyclopropyl-4-[4-(methylsulphonyl)-1,3-benzodioxol-5-oyl]isoxazole (compound 20) as a peach solid, m.p. 178°–180° C.

EXAMPLE 4

A solution of 2-t-butyl-4-chloro-7-(3-cyclopropyl-2-ethoxymethylene-1,3-dioxoprop-1-yl)-benzoxazole (3.3 g), hydroxylamine hydrochloride (0.74 g) and anhydrous sodium acetate (0.73 g) in ethanol was stirred for 2 hours. Water was added and the mixture extracted with ether. The extract was washed with water, dried (magnesium sulphate) and evaporated. Purification by chromatography on silica gel eluting with hexane/ethyl acetate gave 4-(2-t-butyl-4-chlorobenzoxazol-7-oyl)-5-cyclopropylisoxazole (compound 7, 0.15 g) as a cream solid, m.p. 166°–168° C.

By proceeding in a similar manner the following compounds were prepared:

4-(4-chloro-3-methoxybenzo[b]thien-5-oyl)-5-cyclopropylisoxazole (compound 8), as a yellow gum NMR, (CDCl$_3$) $\delta$1.23(2H,m), 1.34(2H,m), 2.67(1H,m), 4.0(3H,s), 6.5(1H,s), 7.3(1H,d), 7.73(1H,d), 8.17(1H, s);

5-cyclopropyl4-(2,2-difluoro-4-methylsulphenyl-1,3 -benzodioxol-5-oyl)isoxazole (compound 10) as an orange gum, NMR (CDCl$_3$) $\delta$1.25(2H,m), 1.35(2H,m), 2.6(3H,s), 2.75(1H,m), 7.05(1H,d), 7.23(1H,d), 8.25(1H,s).

EXAMPLE 5

A solution of 5-cyclopropyl-4-(2,2-difluoro-4-methylsulphinyl-1,3-benzodioxol-5-oyl)isoxazole (1.0 g) in dichloromethane was stirred with m-chloroperbenzoic acid (55%, 1.33 g) for 5 hours, then washed in turn with sodium metabisulphite solution, saturated sodium bicarbonate solution and water. The solution was dried (magnesium sulphate), evaporated to dryness and the residue recrystallised from toluene/cyclohexane to give 5-cyclopropyl-4-(2,2 -difluoro-4-methylsulphonyl-1,3-benzodioxol-5-oyl)isoxazole (compound 6, 0.94 g) as a colourless solid, m.p. 162°–163° C.

By proceeding in a similar manner the following compounds were prepared:

5-cyclopropyl-4-(2,2-difluoro-4-methylsulphinyl-1,3-benzodioxol-5-oyl)isoxazole (compound 9) as a colourless solid, m.p. 162°–164° C.

5-cyclopropyl-4-[5-(methylsulphinyl)-1,4-benzodioxan-6-carbonyl]isoxazole (compound 21) as a cream solid, m.p. 135°–136° C.

5-cyclopropyl-4-[4-(methylsulphinyl)-1,3-benzodioxol-5-oyl]isoxazole (compound 22) as a cream solid, m.p. 171°–173° C.

EXAMPLE 6

A solution of 5-cyclopropyl-4-(4-chloro-3-methoxybenzo[b]thien-5-oyl)isoxazole (0.28 g) in dichloromethane was treated with m-chlorobenzoic acid (55%, 0.72 g). After 18 hours the mixture was cooled to −20° C., filtered and washed with 0.5M sodium bisulphite and water, dried over anhydrous magnesium sulphate and evaporated. Purification by chromatography on silica gel eluting with cyclohexane/ether gave 5-cyclopropyl-4-(4-chloro-3methoxybenzo[b]thien-5-oyl)isoxazole-1,1-dioxide (compound 23, 0.19 g) as a white solid, m.p. 215°–217° C.

By proceeding in a similar manner the following compounds were prepared:

5-cyclopropyl-4-(3,4-dimethoxybenzo[b]thien-5-oyl) isoxazole-1,1 -dioxide (compound 24) as a white solid, m.p. 73°–77° C.

5-cyclopropyl-4-(4-chloro-3-methoxy-2-methylbenzo[b] thien-5-oyl)isoxazole-1,1-dioxide (compound 25) as a white solid, m.p. 143°–144° C.

Reference Example 1

A solution of 4-(3-cyclopropyl-1,3-dioxoprop-1-yl)-2,2-difluoro-1,3-benzodioxole (12.0 g) in dry toluene was treated with N,N-dimethylformamide dimethyl acetal and the mixture stirred overnight. After evaporation in vacuo and re-evaporation after addition of toluene the residue was recrystal from cyclohexane-ethanol to give 4-(3-cyclopropyl-2-dimethylaminomethylene-1,3-dioxopropyl)-2,2 -difluoro-1,3-benzodioxole (6.5 g) as a pale yellow solid, m.p. 118°–119° C.

By proceeding in a similar mariner the following compounds were prepared:

4-(3-cyclopropyl-2-dimethylaminomethylene-1,3-dioxopropyl)-2,2 -difluoro-7-methylsulphenyl-1,3-benzodioxole as an orange gum.

4-(3-cyclopropyl-2-dimethylaminomethylene-1,3-dioxopropyl)-1 -methylsulphonylindole as a brown glass.

5-(3-cyclopropyl-2-dimethylaminomethylene-1,3-dioxopropyl)-4 -methyl-1,3-benzodioxole as a brown gum.

5-(3-cyclopropyl-2-dimethylaminomethylene-1,3-dioxopropyl)-4 -(methylsulphonylmethyl)-1,3-benzodioxole as a brown gum.

5-(3-cyclopropyl-2-dimethylaminomethylene-1,3-dioxopropyl)-2,2 -difluoro-4-(methylsulphonylmethyl)-1,3-benzodioxole as an orange glass, NMR (CDCl$_3$) δ0.7 (2H,m), 1.0(2H,m), 2.1(1H,m), 2.7(3H,m), 3.0(3H,s), 3.2(3H,m), 5.0(2H,s), 7.1(1H,d), 7.4(1H,d), 7.6(1H,s).

5-(3-cyclopropyl-2-dimethylaminomethylene-1,3-dioxopropyl)-4 -(methylsulphonyl)-1,3-benzodioxole as an orange oil.

6-(3-cyclopropyl-2-dimethylaminomethylene-1,3-dioxopropyl)-1,4 -benzodioxan as an orange gum.

Reference Example 2

A solution of 4-(3-cyclopropyl-2-t-butyloxycarbonyl-1,3-dioxoprop-1-yl)-2,2-difluoro-7-methylsulphenyl-1,3-benzodioxole (10.3 g) and para-toluenesulphonic acid (0.5 g) was heated under reflux with toluene for 3 hours. After cooling, the solvent was evaporated in vacuo, and ethyl acetate added. The solution was washed with water, dried over anhydrous magnesium sulphate and evaporated. The residue was purified by column chromatography, eluting with ethyl acetate/cyclohexane to yield 4-(3-cyclopropyl-1,3-dioxoprop-1-yl)-2,2 -difluoro-7-methylsulphenyl-1,3-benzodioxole (6.61 g) m.p. 117.5°–118.5° C.

By proceeding in a similar manner the following compounds were prepared:

4-(3-cyclopropyl-1,3-dioxoprop-1-yl)-2,2-difluoro-1,3-benzodioxole, m.p. 46°–47° C.

2-t-butyl-4-chloro-7-(3-cyclopropyl-1,3-dioxoprop-1-yl) benzoxazole as a yellow oil, NMR(CDCl$_3$) δ1.1(2H, m), 1.25(2H,m), 1.55(9H,s), 1.85(1H,m), 6.7(1H,s), 7.4(1H,d), 7.95(1H,d), 16.3(1H,brs).

7-(3-cyclopropyl-1,3-dioxopropyl)-4-fluoro-1,3-benzoxazol-2-one as an orange glass, NMR(CDCl$_3$) δ0.95(2H, m), 1.05(2H,m), 1.75(1H,m), 6.5(1H,s), 6.8(1H,t), 7.5(1H,dd), 12.0(1H,brs), 16.2(1H,brs).

5-(3-cyclopropyl-1,3-dioxoprop-1-yl)-2,2-difluoro-4-methylsulphenyl-1,3 -benzodioxole, NMR(CDCl$_3$) δ1.05(2H,m), 1.25(2H,m), 1.75(1H,m), 2.05(3H,s), 6.0(1H,s), 7.0(1H,d), 7.45(1H,d), 16.3(1H,brs).

4-chloro-5-(3-cyclopropyl-1,3-dioxoprop-1-yl)-3-methoxybenzo[b]thiophene as a red oil, NMR(CDCl$_3$) δ1.0(2H,m), 1.24(2H,m), 1.76(1H,m), 3.96(3H,s), 6.14(1H,s), 6.46(1H,s), 7.46(1H,d), 7.66(1H,d), 15.9(1H,brs).

2-t-butyl-4-methylsulphenyl-7-(3-cyclopropyl-1,3-dioxoprop-1-yl)benzoxazole, as a yellow solid, NMR (CDCl$_3$) δ1.05(2H,m), 1.25(2H,m), 1.57(9H,s), 1.88(1H,m), 2.67(3H,s), 6.70(1H,s), 7.16(1H,d), 7.92(1H,d).

4-chloro-5-(3-cyclopropyl-1,3-dioxoprop-1-yl)-3-methoxy-2methylbenzo[b]thiophene as a red oil, NMR (CDCl$_3$) δ1.1(2H,m), 1.3(2H,m), 1.8(1H,m), 2.5(3H,s), 3.9(3H,s), 6.1(1H,s), 7.4(1H,d), 7.6(1H,d), 16.0(1H, bs).

4-chloro-5-(3-cyclopropyl-1,3-dioxoprop-1-yl)-3-ethoxybenzo[b]thiophene as an orange gum, NMR (CDCl$_3$) δ 1.0(2H,m), 1.2(2H,m), 1.5(3H,t), 1.7(1H, m), 4.1(2H,q), 6.1(1H,s), 6.4(1H,s), 7.4(1H,d), 7.6(1H, d), 16.0(1H,bs); and 4-chloro-5-(3 -cyclopropyl-1,3-dioxoprop-1-yl)-3-ethoxy-2-ethylbenzo[b]thiophene as an orange gum, NMR (CDCl$_3$) δ1.0(2H,m), 1.2(2H,m), 1.3(3H,t), 1.4(3H,t), 1.7(1H,m), 2.9(2H,q), 4.0(2H,q), 6.1(1H,s), 7.3(1H,d), 7.6(1H,d), 15.9(1H,bs) each having been purified separately from the reaction with the mixture of compounds obtained in Reference Example 3.

5-(3-cyclopropyl-1,3-dioxoprop-1-yl)-3-ethoxy-4-(methylsulphenyl)benzo[b]thiophene as a yellow gum, NMR (CDCl$_3$) δ1.0(2H,m), 1.2(2H,m), 1.6(3H,t), 1.7(1H,m), 2.5(3H,s), 4.2(2H,q), 6.0(1H,s), 6.5(1H,s), 7.4(1H,d), 7.7(1H,d), 16.0(1H,bs).

4-(3-cyclopropyl-1,3-dioxoprop-1-yl)-1-(methylsulphenyl)indole as a brown solid, NMR (CDCl$_3$) δ1.0(2H, m), 1.3(2H,m), 1.8(1H,m), 3.1(3H,s), 6.3(1H,s), 7.2–7.6 (3H,m), 7.7(1H,d), 8.1(1H,d).

5-(3-cyclopropyl-1,3-dioxopropyl)-4-methyl-1,3-benzodioxole as an orange gum, NMR (CDCl$_3$) δ0.9(2H,m), 1.1(2H,m), 1.7(1H,m), 2.3(3H,s), 5.9(1H,s), 6.0(2H,s), 6.6(1H,d), 7.1(1H,d).

5-(3-cyclopropyl-1,3-dioxopropyl)-4-(methylsulphonylmethyl)-1,3-benzodioxole as a brown gum, NMR (CDCl$_3$) δ1.0(2H,m), 1.2(2H,m), 1.7(1H,m), 2.9(3H,s), 4.9(2H,s), 6.10(1H,s), 6.12(2H,s), 6.9(1H,d), 7.3(1H, d).

5-(3-cyclopropyl-1,3-dioxopropyl)-2,2-difluoro-4-(methylsulphonylmethyl)-1,3 -benzodioxole as an orange gum, NMR (CDCl$_3$) δ1.0 (2H,m), 1.3(2H,m), 1.7(1H, m), 2.9(3H,s) 4.9(2H,s), 6.1(1H,s) 7.2(1H,d), 7.5(1H, d).

5-(3-cyclopropyl-1,3-dioxopropyl)-4-(methylsulphonyl)-1,3-benzodioxole as an orange oil, NMR (CDCl$_3$) δ1.0(2H,m), 1.2(2H,m), 1.7(1H,m), 2.5(3H,s), 6.0(1H, s), 6.1(2H,s), 6.7(1H,d), 7.1(1H,d).

6-(3-cyclopropyl-1,3-dioxopropyl)-5-(methylsulphonyl)-1,4-benzodioxan as an orange oil, NMR (CDCl$_3$) δ1.0(2H,m), 1.2(2H,m), 1.7(1H,m), 2.4(3H,s), 4.3(4H, m), 6.0(1H,s), 6.9(1H,d), 7.1(1H,d).

Reference Example 3

A solution of t-butyl-3-cyclopropyl-3-oxopropanoate (5.52 g) in methanol was treated with magnesium turnings (0.72 g) and the reaction initiated by addition of carbon tetrachloride (2 ml). After stirring at ambient temperature for 40 minutes, the solvent was evaporated, and re-evaporated after addition of toluene. The resultant solid was suspended in acetonitrile and a solution of 2,2 -difluoro-7-methylsulphenyl-1,3-benzodioxol-4-oyl chloride (7.9 g) in acetonitrile added. This mixture was stirred overnight, and treated with hydrochloric acid. After stirring for 1.5 hours, extraction with ethyl acetate followed by washing with brine, drying over anhydrous magnesium sulphate, and re-evaporation gave 4-(3-cyclopropyl-2 -t-butyloxycarbonyl-1,3-dioxoprop-1-yl)-2,2-difluoro-7-methylsulphenyl-1,3-benzodioxole (10.3 g) as a yellow oil.

By proceeding in a similar manner the following compounds were prepared:

4-(3-cyclopropyl-2-t-butyloxycarbonyl-1,3-dioxoprop-1-yl)-2,2 -difluoro-1,3-benzodioxole.

2-t-butyl-4-chloro-7-(3-cyclopropyl-2-t-butyloxycarbonyl-1,3 -dioxoprop-1-yl)benzoxazole.

7-(3-cyclopropyl-2-t-butyloxycarbonyl-1,3-dioxoprop-1-yl)-4-fluoro-1,3-benzoxazol-2-one.

5-(3-cyclopropyl-2-t-butyloxycarbonyl-1,3-dioxoprop-1-yl)-2,2-difluoro-4 -methylsulphenyl-1,3-benzodioxole.

4-chloro-5-(3-cyclopropyl-2-t-butyloxycarbonyl-1,3-dioxoprop-1-yl)3 -methoxybenzo[b]thiophene.

2-t-butyl-4-methylsulphenyl-7-(3-cyclopropyl-2-t-butyloxycarbonyl-1,3 -dioxoprop-1-yl)benzoxazole.

4-chloro-5-(3-cyclopropyl-2-t-butyloxycarbonyl-1,3-dioxoprop-1-yl)-3 -methoxy-2-methylbenzo[b]thiophene.

A mixture of 4-chloro-5-(3-cyclopropyl-2-t-butyloxycarbonyl-1,3-dioxoprop-1-yl)-3 -ethoxybenzo[b]thiophene and 4-chloro-5-(3 -cyclopropyl-2-t-butyloxycarbonyl-1,3-dioxoprop-1-yl)-3-ethoxy-2 -ethylbenzo[b]thiophene (prepared from the product of reference example 17).

5-(3-cyclopropyl-2-t-butyloxycarbonyl-1,3-dioxoprop-1-yl-3-ethoxy-4-(methylsulphenyl)benzo[b]thiophene.

4-(3-cyclopropyl-2-t-butyloxycarbonyl-1,3-dioxoprop-1-yl)-1 -methylsulphonyl)indole.

5-(3-cyclopropyl-2-t-butyloxycarbonyl-1,3-dioxoprop-1-yl)-4 -ethyl-1,3-benzodioxole.

5-(3-cyclopropyl-2-t-butyloxycarbonyl-1,3-dioxoprop-1-yl)-4 -(methylsulphonylmethyl)-1,3-benzodioxole.

5-(3-cyclopropyl-2-t-butyloxycarbonyl-1,3-dioxoprop-1-yl)-2,2-difluoro-4 -(methylsulphonylmethyl)-1,3-benzodioxole.

5-(3-cyclopropyl-2-t-butyloxycarbonyl-1,3-dioxoprop-1-yl)-4 -(methylsulphenyl)-1,3-benzodioxole.

6-(3-cyclopropyl-2-t-butyloxycarbonyl-1,3-dioxoprop-1-yl)-5 -(methylsulphenyl)-1,4-benzodioxan.

Reference Example 4

2,2-Difluoro-1,3-benzodioxole-4-carboxylic acid (15.0 g) was dissolved in 1,2-dichloroethane and N,N-dimethylformamide and thionyl chloride (10.6 g) added. The mixture was heated under reflux for 1 hour, and the solvent evaporated in vacuo. The residue was dissolved in toluene and re-evaporated to yield 2,2-difluoro-1,3 -benzodioxol-4-oyl chloride (17.35 g).

By proceeding in a similar manner 2,2-difluoro-7 -methylsulphenyl-1,3-benzodioxol-4-oyl chloride was prepared.

Reference Example 5

A solution of n-butyllithium (88ml of 2.5M solution in hexane) was diluted with dry hexane under an inert atmosphere, cooled to 5° C. and N,N,N', N'-tetramethylethylenediamine (33 ml) in dry hexane added dropwise. Dry tetrahydrofuran was added at −35° C., the mixture cooled to −70° C. and 2,2-difluoro-1,3-benzodioxole-4-carboxylic acid (20.2 g) in dry tetrahydrofuran added during 1.5 hours keeping the temperature below −62° C. After 20 hours at −75° C., dimethyldisulphide (25 ml) was added during 30 minutes, and the mixture stirred at that temperature overnight and then at room temperature for 24 hours.

The mixture was poured into ice water, washed with ether and acidified to pH 1 with conc. hydrochloric acid. This was extracted with ether, the extracts washed with brine and dried over anhydrous magnesium sulphate. Evaporation of the solvent gave 2,2-difluoro-7 -methylsulphenyl-1,3-benzodioxole-4-carboxylic acid (17.75 g) NMR (D$_6$ DMSO); δ7.65 (1H,d), 7.25 (1H,d), 2.6 (3H,s).

2,2-Difluoro-1,3-benzodioxole-4-carboxylic acid is described in European Patent Publication No. 0333658.

Reference Example 6

A mixture of 5-(3-cyclopropyl-1,3-dioxoprop-1-yl)-3,4-dimethoxybenzo[b]thiophene (0.5 g) and triethyl orthoformate (0.73 g) was heated under reflux with acetic anhydride (10 ml) for 3 hours. After cooling and addition of toluene the solution was evaporated to dryness to yield 5-(3-cyclopropyl-2-ethoxymethylene-1,3-dioxoprop-1-yl)-3,4-dimethoxybenzo[b]thiophene as a red oil.

By proceeding in a similar manner the following compounds were prepared:

5-(3-cyclopropyl-2-ethoxymethylene-1,3-dioxoprop-1-yl)benzo- 1,2,3-thiadiazole.

2-t-butyl-4-chloro-7-(3-cyclopropyl-2-ethoxymethylene-1,3 -dioxoprop-1-yl)benzoxazole as an orange oil.

5-(3-cyclopropyl-2-ethoxymethylene-1,3-dioxoprop-1-yl)-2,2-difluoro-4-methylsulphenyl-1,3-benzodioxole.

4-chloro-5-(3-cyclopropyl-2-ethoxymethylene-1,3-dioxoprop-1-yl)-3-methoxybenzo[b]thiophene.

2-t-butyl-4-methylsulphenyl-7-(3-cyclopropyl-2-ethoxymethylene-1,3-dioxoprop-1-yl)benzoxazole.

4-chloro-5-(3-cyclopropyl-2-ethoxymethylene-1,3-dioxoprop-1-yl)-3-methoxy-2-methylbenzo[b]thiophene.

4-chloro-5-(3-cyclopropyl-2-ethoxymethylene-1,3-dioxoprop-1 -yl)-3-ethoxy-2-ethylbenzo[b]thiophene.

5-(3-cyclopropyl-2-ethoxymethylene-1,3-dioxoprop-1-yl)-3 -ethoxy-4-methylsulphenylbenzo[b]thiophene.

4-chloro-5-(3-cyclopropyl-2-ethoxymethylene-1,3-dioxoprop-1-yl)-3 -ethoxybenzo[b ]thiophene.

Reference Example 7

A solution of methyl 4-chloro-3-methoxybenzo[b] thiophene-5-carboxylate (3.95 g) in dry tetrahydrofuran was added to sodium hydride (60%, 1.355 g) and stirred under an inert atmosphere with warming to 50°–60° C. Cyclopropyl methyl ketone (2.59 g) was added with stirring at 50°–60° C. for 3 hours. After this time the reaction exothermed and was heated at 50°–60° C. for a further 1.5 hours. After cooling, isopropanol (5 ml) was cautiously added, followed by water (5 ml). The mixture was poured onto 2N hydrochloric acid and extracted with ether. The ether extracts were dried over anhydrous magnesium sulphate and evaporated in vacuo. The residue was purified by column chromatography on silica gel, eluting with ether/cyclohexane to yield 5-(3-cyclopropyl-1,3-dioxoprop-1 -yl)-3,4-dimethoxybenzo[b] thiophene as a yellow solid (1.47 g), m.p. 77.5°–80° C.

By proceeding in a similar manner there was obtained 5-(3 -cyclopropyl-1,3-dioxoprop-1-yl)benzo-1,2,3-thiadiazole, as a pale orange solid, m.p. 141.5°–144.5° C.

Reference Example 8

A mixture of 4-chloro-3-hydroxybenzo[b]thiophene-5-carboxylic acid (23.4 g), caesium carbonate (70.07 g), methyl iodide (50 ml) and tetra-n-butylammonium iodide (1.89 g) was heated in acetone at reflux overnight. The solvent was evaporated and the residue dissolved in ethyl acetate. The solution was washed with saturated sodium carbonate solution, water, dried over anhydrous magnesium sulphate, and evaporated in vacuo. The residue was purified by column chromatography eluting with ethyl acetate/petroleum ether, b.p. 60°–80° C. to yield methyl 4-chloro-3methoxybenzo[b]thiphene-5 -carboxylate (8.35 g) as a pale yellow solid, m.p. 67°–70°C. and methyl 4-chloro-3-methoxy-2-methylbenzo[b]thiophene-5-carboxylate (3.4 g), NMR (CDCl$_3$) δ2.5(3H,s), 3.9(3H,s), 4.0(3H,s), 7.6(2H,s).

Reference Example 9

A mixture of dimethyl 4-chloro-3-hydroxybenzo[b]thiophene-2,5 -dicarboxylate (12.62 g) and 2N sodium hydroxide was heated under reflux for 2 hours. The mixture was neutralised with 2N hydrochloric acid whilst still at 100° C. The solution was acidified with concentrated hydrochloric acid and stirred under reflux conditions for a further 30 minutes. A purple solid (7.72 g) was filtered and dried in a dessicator and shown to be 4-chloro-3-hydroxybenzo[b]thiophene-5-carboxylic acid, NMR (DMSO D$_6$) δ 6.67 (1H,s), 7.54 (1H,d), 7.87 (1H,d), 10.3 (1H,s), 13.34 (1H,s) and 4.07 (2H,s), 7.63 (1H,d), 7.93 (1H,d), 13.34 (1H,s) (40% in the keto form).

Reference Example 10

Dimethyl 2,4-dichloroisophthaloate (11.95 g) and methyl thioglycolate (7.23 g) was dissolved in N,N-dimethylformamide, and lithium hydroxide monohydrate (3.81 g) added. The mixture was stirred at ambient temperature for 2 days, diluted with water and brought to pH 1 with hydrochloric acid. The solid was filtered, washed with boiling cyclohexane and dried by azeotropic removal of toluene to give dimethyl 4-chloro-3-hydroxybenzo[b]thiophene-2,5-dicarboxylate (13.44 g) as a beige solid, m.p. 127°–131° C.

Reference Example 11

2,4-Dichloro-3-methoxycarbonylbenzoylchloride (34.76 g) was stirred and heated under reflux with methanol for 15 hours. After cooling, the solvent was evaporated and the residue recrystallised from cyclohexane to give dimethyl 2,4-dichloroisophthaloate (16.04 g) as a beige solid, NMR (DMSO D$_6$) δ3.87 (3H,s), 3.94 (3H,s), 7.74 (1H,d), 7.94 (1H,d).

Reference Example 12

2,4-Dichloro-3-methoxycarbonylbenzoic acid (32.37 g) and thionyl chloride (100 ml) was heated under reflux with stirring for 3 hours. The mixture was cooled and evaporated in vacuo, then re-evaporated after addition of toluene to give 2,4-dichloro-3-methoxycarbonylbenzoyl chloride (34.76 g) as a dark brown oil. This was used in the next stage without purification.

Reference Example 13

To a stirred solution of diisopropylamine (22 ml) in dry tetrahydrofuran (160 ml) cooled to 0° C. under an inert atmosphere was added n-butyl lithium (2.5M, 67 ml) dropwise. The solution was stirred for 30 minutes at 0° C., then added to a solution of methyl 2,6-dichlorobenzoate (26.62 g) in dry tetrahydrofuran (160 ml) cooled to −78° C. under an inert atmosphere. After 1.5 hours at this temperature the mixture was poured onto excess solid carbon dioxide and left to stand overnight. The solvent was evaporated in vacuo and the residue acidified with 2N hydrochloric acid. This was then extracted with ethyl acetate, dried over anhydrous magnesium sulphate and evaporated in vacuo to yield 2,4-dichloro-3-methoxycarbonylbenzoic acid (32.37 g) as a solid, NMR (DMSO D$_6$) δ3.93 (3H,s), 7.70 (1H, d), 7.91 (1H,d).

Reference Example 14

A solution of ethyl 3-amino-4-benzylthiobenzoate (6.11 g) in ethanol (20 ml) was added to a vigorously stirred solution of sodium nitrite (3.23 g) and 48% hydrobromic acid (21 ml) in water (2500 ml) cooled to 0° C. The mixture was allowed to warm to room temperature overnight, and was made basic with solid sodium carbonate (12 g). The red precipitate was faltered, dissolved in ethyl acetate, dried over anhydrous magnesium sulphate and evaporated to yield ethyl benzo-1,2,3-thiadiazole-5-carboxylate (2.97 g) as a red crystalline solid, m.p. 74.5°–77° C.

Reference Example 15

Ethyl 4-benzylthio-3-nitrobenzoate (10.16 g) was suspended in ethanol and stirred. Concentrated hydrochloric acid (60 ml) was added, followed by iron powder (12.51 g) portionwise. The mixture was warmed slowly to 60°–70° C. and stirred overnight. After cooling the mixture was poured onto ice, neutralised with solid sodium bicarbonate and filtered. The solid was continuously extracted with ethyl acetate, and the filtrate extracted with ethyl acetate. The extracts were dried over anhydrous magnesium sulphate, and evaporated to yield ethyl 3-amino-4-benzylthiobenzoate (6.11 g) as an oil, NMR (CDCl$_3$) δ1.37 (3H, t), 3.97 (2H,s), 4.33 (2H,q), 7.1–7.4 (8H).

Reference Example 16

Ethyl 4-chloro-3-nitrobenzoate (10 g) and benzyl mercaptan (5.41 g) were dissolved in N,N-dimethylformamide and whilst stirring, lithium hydroxide monohydrate (1.83 g) was added. The mixture was stirred overnight then poured into ether and 2N hydrochloric acid. The organic phase was washed with water, dried over anhydrous magnesium sulphate and evaporated to yield ethyl 4-benzylthio-3-nitrobenzoate (10.16 g), obtained as an oil, NMR (CDCl$_3$) δ1.41 (3H, t), 4.24 (2H,s), 4.40 (2H,q), 7.3–7.47 (5H), 7.53 (1H,d), 8.14 (1H,dd), 8.86 (1H,d).

Reference Example 17

A stirred suspension of 4-fluoro-1,3-benzoxazol-2-one-7-carboxylic acid (1.79 g) in dry dichloromethane was treated with oxalyl chloride (0.97 g), followed by N,N-dimethylformamide (3 drops) to initiate the reaction. Stirring was maintained under reflux conditions for 1.5 hours and the mixture evaporated to dryness to give 4-fluoro-1,3-benzoxazol-2-one-7-carboxylic acid chloride, used in the next stage without purification.

Similarly prepared were the following: 2-t-butyl-4-chlorobenzoxazole-7-carboxylic acid chloride as an orange solid, used directly in the next stage.

2,2-difluoro-4-methylsulphenyl-1,3-benzodioxole-5-carboxylic acid chloride, obtained as an orange semi-solid.

4-chloro-3-methoxybenzo[b]thiophene-5-carboxylic acid chloride.

2-t-butyl-4-methylsulphenylbenzoxazole-7-carboxylic acid chloride.

4-chloro-3-methoxy-2-methylbenzo[b]thiophene-5-carboxylic acid chloride as a yellow solid.

A mixture of 4-chloro-3-ethoxybenzo[b]thiophene-5-carboxylic acid chloride and 4-chloro-3-ethoxy-2-ethylbenzo[b]thiophene-5-carboxylic acid chloride (prepared from the product of reference example 18).

3-ethoxy-4-methylsulphenylbenzo[b]thiophene-5-carboxylic acid chloride as a brown liquid.

1-(methylsulphonyl)indole-4-carboxylic acid chloride as a yellow solid.

4-methyl-1,3-benzodioxole-5-carboxylic acid chloride as an orange solid.

4-(methylsulphonylmethyl)-1,3-benzodioxole-5-carboxylic acid chloride as a brown gum.

2,2-difluoro-4-(methylsulphonylmethyl)-1,3-benzodioxole-5-carboxylic acid chloride as a yellow solid.

4-(methylsulphenyl)-1,3-benzodioxole-5-carboxylic acid chloride as a beige solid.

5-(methylsulphenyl)-1,4-benzodioxan-6-carboxylic acid chloride as an orange oil.

4-Fluoro-1,3-benzoxazol-2-one-7-carboxylic acid is described in *Synthetic Communications*, 1990, 20, 1423 by D. R. Reavill and S. K. Richardson.

Reference Example 18

A mixture of methyl 4-chloro-3-methoxybenzo[b]thiophene-5-carboxylate (8.35 g) and lithium hydroxide hydrate (1.37 g) was stirred in methanol (75 ml) and water (25 ml) at room temperature for 4 days. The methanol was evaporated in vacuo and the mixture poured onto excess cold dilute hydrochloric acid. The solid was filtered, washed with cold cyclohexane and dried to give 4-chloro-3-methoxybenzo[b]thiophene-5-carboxylic acid (7.28 g) as a white solid, NMR ($d_6$ DMSO) $\delta 3.9(3H,s)$, 7.0(1H,s), 7.6(1H,d), 7.95(1H,d), 13.3(1H,brs).

Similarly prepared was the following:
4-chloro-3-methoxy-2-methylbenzo[b]thiophene-5-carboxylic acid as a pale yellow solid, m.p. 185°–192° C.

Similarly prepared was the following:
2-t-butyl-4-methylsulphenylbenzoxazole-7-carboxylic acid, m.p. 203°–204° C., using potassium hydroxide instead of lithium hydroxide hydrate.

Similarly prepared from the product of reference example 24, a mixture of ethyl 4-chloro-3-ethoxybenzo[b]thiophene-5 -carboxylate and ethyl 4-chloro-3-ethoxy-2-ethylbenzo[b]thiophene, using lithium hydroxide in ethanol, tetrahydrofuran and water was obtained a mixture of 4-chloro-3-ethoxybenzo[b]thiophene-5-carboxylic acid and 4-chloro-3-ethoxy-2-ethylbenzo[b]thiophene-5-carboxylic acid as a white solid.

Similarly prepared by this revised method was 3-ethoxy-4-(methylsulphenyl)benzo[b]thiophene-5-carboxylic acid as a brown solid, NMR (CDCl$_3$) $\delta 1.6(3H, t)$, 2.6(3H,s), 4.2(2H, q), 6.5(1H,s), 7.8(1H,d), 8.2(1H,d).

Similarly prepared was the following:
1-(methylsulphenyl)indole-4-carboxylic acid as a white solid, m.p. 220°–222° C., using potassium hydroxide in industrial methylated spirits instead of lithium hydroxide hydrate in methanol.

By this revised method was also prepared the following:
4-(methylsulphonylmethyl)-1,3-benzodioxole-5-carboxylic acid as an orange gum, NMR (CDCl$_3$) $\delta 2.7(3H, s)$, 4.9(2H,s), 6.0(2H,s), 6.7(1H,d), 7.6(1H,d).

Reference Example 19 n-Butyllithium (11.6ml of a 2.5M solution in hexanes) was added dropwise to a stirred solution of 2,2-difluoro-1,3-benzodioxole-5-carboxylic acid (2.8 g) in dry, tetrahydrofuran maintained at –78° C. under an inert atmosphere. After 6 hours at –78° C., a solution of dimethyl disulphide (3.75 ml) was added dropwise and the mixture left to reach room temperature overnight. Sodium hydroxide solution (2M) was added, the mixture washed 10 with ether, acidified (hydrochloric acid) and the precipitated solid filtered. This was washed (hexane) and dried to give 2,2-difluoro-4 -methylsulphenyl-1,3-benzodioxole-5-carboxylic acid (2.59 g) as a cream solid. A pure sample was obtained as colourless crystals m.p. 190°–192° C. by recrystallisation from toluene/cyclohexane.

Similarly prepared were the following:
4-(methylsulphenyl)-1,3-benzodioxole-5-carboxylic acid as a cream solid, m.p. 196°–198° C.

5-(methylsulphenyl)-1,4-benzodioxan-6-carboxylic acid as a cream solid, m.p. 122°–124° C.

1,4-benzodioxan-6-carboxylic acid is described in G. Coudert et al, *Tetrahedron Letters*, 1978, 1059.

Reference Example 20 n-Butyl lithium (101.6 ml of a 2.5M solution in hexane) was added during 30 minutes to a stirred solution of 2,5-dichloro-1-(trimethylacetylamino)benzene (25.0 g) in dry tetrahydrofuran at –40° C. and the solution stirred at –20° C. for 1.5 hours and poured onto solid carbon dioxide in dry tetrahydrofuran. The mixture was allowed to reach room temperature, 2M sodium hydroxide solution added and extracted with ethylacetate. The aqueous solution was acidified (concentrated hydrochloric acid) and the precipitated solid collected and dried to give 2-t-butyl-4-chlorobenzoxazole-7-carboxylic acid (1 1.7 g) m.p. 209°–210° C.

Reference Example 21

To a stirred mixture of 2,5-dichloroaniline (15.0 g), triethylamine (dry 14.1 ml) and 4-dimethylaminopyridine (0.45 g) in dry dichloromethane (100 ml) was added a solution of di-t-butyldicarbonate (22.2 g) in dry dichloromethane. The mixture was stirred under nitrogen for 18 hours and quenched by the addition of saturated ammonium chloride solution and extracted with dichloromethane. The extract was dried (magnesium sulphate), evaporated and purified by chromatography on silica gel eluting with cyclohexane to give 2,5-dichloro-1-(trimethylacetylamino)benzene (12.2 g) as a cream solid, used in the next stage without purification.

Reference Example 22

A mixture of methyl 2-t-butyl-4-chloro-1,7-benzoxazole-7-carboxylate (5.7 g) and sodium thiomethoxide (1.64 g) was stirred at reflux for 48 hours in dry tetrahydrofuran. Water was added and the mixture extracted (ether), dried (anhydrous magnesium sulphate) and evaporated. Purification by chromatography on silica gel gave methyl 2-t-butyl- 4-methylsulphenyl-1,3-benzoxazole-7-carboxylate (2.8 g) as a cream solid, NMR(CDCl₃) δ1.53(9H,s), 2.64(3H,s), 3.98(3H,s), 7.09(1H,d), 7.85(1H,d).

Similarly prepared was the following:

Ethyl 3-ethoxy-4-methylsulphenylbenzo[b]thiophene-5-carboxylate, as a yellow gum, NMR (CDCl₃) δ1.4(3H, t), 1.6(3H, t), 2.5(3H,s), 4.2(2H,q), 4.4(2H,q), 6.5(1H, s), 7.4(1H,d), 7.7(1H, By proceeding in a similar manner, performing the reaction at room temperature, the following compounds were prepared:

Methyl 4-(methanesulphenylmethyl)-1,3-benzodioxole-5-carboxylate as a yellow oil, NMR (CDCl₃) δ2.1(3H, s), 3.9(3H,s), 4.1(2H,s), 6.1(2H,s), 6.7(1H,d), 7.6(1H, d).

Methyl 2,2-difluoro-4-(methanesulphenylmethyl)-1,3-benzodioxole-5-carboxylate as a yellow solid, m.p. 64°–66° C.

Reference Example 23

Oxalyl chloride (2.6 ml) was added dropwise to a stirred suspension of 2-t-butyl-4-chloro-1,3-benzoxazole-7-carboxylic acid (6.2 g). Dry N,N-dimethylformamide (3 drops) was added and the mixture stirred at reflux for 2 hours and evaporated. Dichloromethane was added and the solution added dropwise to a stirred solution of methanol (dry, 3.0 ml) and triethylamine (dry, 10 ml) in dichloromethane at 0° C. After stirring at ambient temperature for 18 hours, the mixture was washed with hydrochloric acid (2M) water, sodium carbonate (2M), water, then dried magnesium sulphate) and evaporated to give methyl 2-t-butyl-4-chloro-1,3-benzoxazole-7-carboxylate (5.7 g) as a light brown solid, m.p. 130°–131° C.

Similarly prepared was the following:

Methyl 4-methyl-1,3-benzodioxole-5-carboxylate isolated as a 4:1 mixture with methyl 1,3-benzodioxole-5-carboxylate) as an orange gum.

Methyl 2,2-difluoro4-methyl-1,3-benzodioxole-5-carboxylate as an orange solid, m.p. 39°–41° C.

Reference Example 24

A mixture of 4-chloro-3-hydroxybenzo[b]thiophene-5-carboxylic acid (45.2 g), caesium carbonate (135.4 g), ethyl iodide (247 g) and tetra-n-butylammonium iodide (3.65 g) was heated in acetonitrile at reflux for 18 hours. The solvent was evaporated and the residue partitioned between ethyl acetate and water. The organic phase was washed with water three more times, dried over anhydrous magnesium sulphate and evaporated in vacuo. The residue was purified by column chromatography eluting with ethyl acetate/petroleum ether, b.p. 60°–80° C. obtaining an approximately 5:1 mixture of ethyl 4-chloro-3-ethoxybenzo[b]thiophene-5-carboxylate and ethyl 4-chloro-3-ethoxy-2-ethylbenzo[b]thiophene as a yellow solid (23.0 g).

Reference Example 25

Sodium hydride (1.1 g of a 80% dispersion in mineral oil), methyl 1H-indole 4-carboxylate (5.46 g) and anhydrous acetonitrile were mixed under an inert atmosphere at 0° C. and stirred at room temperature for an hour. Methanesulphonyl chloride (1.8 g) was added at 0° C. and the mixture stirred at room temperature for 18 hours. Methanol and then water were then added and the mixture extracted with dichloromethane. The organic phase was washed with 2N hydrochloric acid, water, 1M sodium carbonate and water, dried over anhydrous magnesium sulphate and evaporated in vacuo. The residue was purified by column chromatography eluting with ethyl acetate/hexane obtaining methyl 1-(methylsulphonyl)indole-4-carboxylate (4.7 g) as a white solid, m.p. 102°–104° C.

Methyl 1H-indole-4-carboxylate is described in A. P. Kozikowski et al, *Journal of Organic Chemistry*, 1980, 45, 3350.

Reference Example 26

A solution of n-butyllithium (5.1 ml of a 2.5M solution in hexanes) was added to a stirred suspension of 1,3-benzodioxole-5-carboxylic acid (1.0 g) in anhydrous tetrahydrofuran under an inert atmosphere keeping the temperature below −60° C. The mixture was then stirred at −78° C. for 7 hours and methyl iodide (0.50 g) added and the mixture stirred at room temperature for 18 hours. The mixture was then treated with water and 2N sodium hydroxide. The aqueous phase was washed with ether, acidified and filtered. The solid was washed with hexane and dried to give 4-methyl-1,3 -benzodioxole-5-carboxylic acid as a cream solid (0.91 g), m.p. 217°–219° C.

By proceeding in a similar manner the following compound was also prepared (from 2,2-difluoro-1,3-benzodioxole-5-carboxylic acid which is described in U.S. Pat. No. 4,895,871) 2,2-difluoro-4 -methyl-1,3-benzodioxole-5-carboxylic acid as a beige solid, m.p. 180°–182° C.

Reference Example 27

A mixture of methyl 4-methyl-1,3-benzodioxole-5-carboxylate (9.9 g), N-bromosuccinimide (9.6 g) in carbon tetrachloride was irradiated with a 500 W medium pressure ultraviolet lamp for six hours at reflux. The mixture was cooled to 0° C., filtered and the filtrate evaporated to give an oil which was crystallised from toluene/hexane and recrystallised from cyclohexane to give methyl 4-bromomethyl-1,3-benzodioxole-5-carboxylate (3.0 g) as a beige solid, m.p. 95°∝98° C.

By proceeding in a similar manner the following compound was prepared:

Methyl 4-bromomethyl-2,2-difluoro-1,3-benzodioxole-5-carboxylate as a yellow solid, m.p. 56°–58° C.

Reference Example 28

A mixture of methyl 4-(methanesulphenylmethyl)-1,3 -benzodioxole-5-carboxylate (1.6 g), m-chloroperbenzoic acid (55%, 4.6 g) and dichloromethane was stirred for 24 hours and then washed with 10% sodium metabisulphite solution, saturated sodium bicarbonate and water, dried over anhydrous magnesium sulphate and evaporated to give methyl 4-(methylsulphonylmethyl)-1,3 benzodioxole-5-carboxylate as a yellow gum (1.5 g), NMR (CDCl₃) δ 2.8(3H, s), 3.8(3H,s), 4.9(2H,s), 6.1(2H,s), 6.8(1H,d), 7.6(1H,d).

Reference Example 29

A mixture of methyl 2,2-difluoro-4-(methanesulphenylmethyl)-1,3 -benzodioxole-5-carboxylate (4.1 g) and cyclopropyl methyl ketone (2.5 g) in anhydrous tetrahydrofuran was slowly added to a refluxing suspension of sodium hydride (0.98 g of a 80% dispersion in mineral oil) in tetrahydrofuran under an inert atmosphere. After a further two hours at reflux the reaction mixture was cooled and methanol (15 ml) added. The mixture was then added to saturated sodium bicarbonate and the inorganic phase was washed with dichloromethane and acidified to pill with concentrated hydrochloric acid. The resulting precipitate was dried in vacuo to give 2,2-difluoro-4-(methylsulphonyl-methyl)-1,3-benzodioxole-5-carboxylic acid (3.3 g) as a yellow solid, m.p. 107°–109° C.

Reference Example 30

35% Hydrogen peroxide (3.1ml) was slowly added to a stirred solution of 2,2-difluoro-4-(methylsulphonylmethyl)-1,3 -benzodioxole-5-carboxylic acid (3.3 g) in glacial acetic acid at 0° C. The mixture was then stirred at 50° C. for 18 hours, cooled and diluted with water, collecting the resulting precipitate by filtration. Drying in vacuo gave 2,2-difluoro-4-(methylsulphonylmethyl)-1,3-benzodioxole-5-carboxylic acid (2.2 g) as a cream solid, m.p. 185°–186° C.

According to a feature of the present invention, there is provided a method for controlling the growth of weeds (i.e. undesired vegetation) at a locus which comprises applying to the locus a herbicidally effective amount of at least one isoxazole derivative of formula I or an agriculturally acceptable salt thereof. For this purpose, the isoxazole derivatives are normally used in the form of herbicidal compositions (i.e. in association with compatible diluents or carriers and/or surface active agents suitable for use in herbicidal compositions), for example as hereinafter described. The compounds of formula I show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutdon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example Alopecurus myosuroides, Avena fauna, Digitaria sanguinalis, Echinochloa crus-galli, Eleusine indica and Setaria spp, e.g. *Setaria faberii* or *Setaria viridis,* and sedges, for example, *Cyperus esculentuns.*

The amounts of compounds of formula I applied vary with the nature of fie weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula I may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula I may be incorporated into the soft in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a pre-emergence control on later-germinating weeds in the soft.

Where especially prolonged weed control is required, the application of the compounds of formula I may be repeated if required.

According to a further feature of the present invention, there are provided compositions suitable for herbicidal use comprising one or more of the isoxazole derivatives of formula I or an agriculturally acceptable salt thereof, in association with, and preferably homogeneously dispersed in, one or more compatible agriculturaly-acceptable diluents or carriers and/or surface active agents [i.e. diluents or carriers and/or surface active agents of the type generally accepted in the art as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or nonionic types, for example sulphoficinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric add esters and sulphonic acids such as dinonyl- and diocryl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25 % by weight in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, grinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an off may be used without further dilution using the electrostatic spray technique.

Herbicidal compositions according to the present invention may also contain if desired, conventional adjuvants such as adhesives, protective colloids, thickeners, penetrating agents, stabilizers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 0% of one or more compounds of formula I, from 2 to 10% of surface-active agent, from 0.1 to 5% of thickener and from 15 to 87.9% of water;

wettable powders which comprise from 10 to 90% of one or more compounds of formula I, from 2 to 10% of surface-active agent and from 8 to 88% of solid diluent or carrier;

water soluble or water dispersible powders which comprise from 10 to 90% of one or more compounds of formula I, from 2 to 40% of sodium carbonate and from 0 to 88% of solid diluent;

liquid water soluble concentrates which comprise from 5 to 50%, e,g. 10 to 30%, of one or more compounds of formula I, from 5 to 25 % of surface-active agent and from 25 to 90%, e.g., 45 to 85 %, of water-miscible solvent, e,g, dimethylformamide, or a mixture of water-miscible solvent and water;

liquid emulsifiable suspension concentrates which comprise from 10 to 70% of one or more compounds of formula I, from 5 to 15% of surface-active agent, from 0.1 to 5% of thickener and from 10 to 84.9% of organic solvent;

granules which comprise from 1 to 90%, e.g. 2 to 10% of one or more compounds of formula I, from 0.5 to 7%, e.g. 0.5 to 2%, of surface-active agent and from 3 to 98.5%, e.g. 88 to 97.5%, of granular carrier; and emulsifiable concentrates which comprise 0.05 to 90%, and preferably from 1 to 60% of one or more compounds of formula I, from 0.01 to 10%, and preferably from 1 to 10%, of surface-active agent and from 9.99 to 99.94 %, and preferably from 39 to 98.99%, of organic solvent.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil[3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)6-ethylamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenylpyrazolium salts], flampropmethyl[methyl N-2-(N-benzoyl-3-chloro-4-fluoroanilino)-propionate], fluometuron [N'-(3-trifluoromethylphenyl)-N,N-dimethylurea], isoproturon [N'-(4-isopropylphenyl)-N,N-dimethylurea], insecticides, e.g. synthetic pyrethroids, e.g. permethrin and ,cypermethrin, and fungicides, e.g. carbamates, e.g. methyl N-(1-t-butyl-carbamoyl-benzimidazol-2-yl)carbamate, and triazoles e.g. 1-(4-chloro-phenoxy)-3,3-dimethyl-1-(1,24-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

In one embodiment of the present invention there is provided a herbicidal composition comprising a herbicidally effective amount of a compound of formula I or an agriculturally acceptable salt thereof, and at least one member of the group consisting of an agriculturally acceptable carrier and an agriculturally acceptable surface active agent, said composition being unfit for human or animal consumption. In such a herbicidal composition, a carrier or diluent can be present which is pharmaceutically unacceptable, and/or a surfactant can be present which is pharmaceutically unacceptable, and/or a further ingredient (such as, for example, a further herbicide, a fungicide or an insecticide) which is pharmaceutically unacceptable can be present in the composition. By "pharmaceutically unacceptable" is meant materials which have toxicity in the mounts/proportions present in the compositions of this embodiment, including not only materials which should be totally avoided in pharmaceutical compositions but also those which are acceptable in human and veterinary medicines at lower levels than the levels at which they are present in these herbicidal compositions, or those materials which are not inherently pharmaceutically unacceptable but which are employed in grades of purity which are unacceptable for human or veterinary consumption (for example, containing higher levels of residues of certain organic solvents than is pharmaceutically acceptable). Of course, the active ingredient of formula I can itself be used in a grade of purity which is pharmaceutically unacceptable in order to provide compositions of this embodiment. The compositions of this embodiment can alternatively be unfit for human or animal consumption because they have been prepared under conditions which do not meet governmental standards for the manufacture of foods and medicines, for example, these compositions can be prepared under less stringent standards which permit higher bacterial levels in the final product than in compositions fit for human or animal consumption.

The following Examples illustrate herbicidal compositions according to the present invention:

EXAMPLE C1

| | |
|---|---|
| Active ingredient (compound 1) | 20% w/v |
| Potassium hydroxide solution 33% w/v | 10% v/v |
| Tetrahydrofurfuryl alcohol (TBFA) | 10% v/v |
| Water | to 100 volumes | by stirring THFA, active ingredient (compound 1) and 90% volume of water and slowly adding the potassium hydroxide solution until a steady pH 7–8 is obtained then making up to volume with water.

Similar soluble concentrates may be prepared as described above by replacing the isoxazole (compound 1) with other compounds of formula I.

EXAMPLE C2

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene | |

| | |
|---|---|
| sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula I.

EXAMPLE C3

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula I.

Representative compounds of formula I have been used in herbicidal applications according to the following procedures.

METHOD OF USE OF HERBICIDAL COMPOUNDS:
a) General

Appropriate quantities of the compounds used to treat the plants were dissolved in acetone to give solutions equivalent to application rates up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in nonsterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | Number of plants per pot | Growth stage |
|---|---|---|
| 1) Broad-leafed weeds | | |
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Sinapis arvensis | 4 | 2 leaves |
| Xanthium strumarium | 1 | 2–3 leaves. |
| 2) Grass weeds | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Cyperus esculentus | 3 | 3 leaves. |
| 1) Broad-leafed | | |
| Crops | | |
| Cotton | 2 | 1 leaf |
| Soya | 2 | 2 leaves. |
| 2) Grass | | |
| Crops | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

When applied either pre- or post-emergence at 4 kg/ha or less, compounds 1 to 27 gave at least 90% control of one or more weed species, and showed selectivity in at least one of the crop species.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula

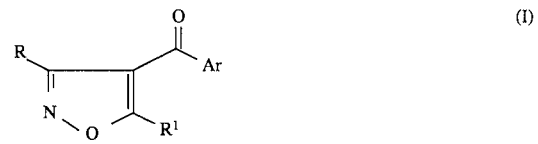

or an agriculturally acceptable salt thereof, wherein:

Ar is a phenyl ring having two substituents on adjacent positions which together with the two ring atoms to which they are attached form a saturated, partially saturated or aromatic carbocyclic or heterocyclic ring having five to seven ring atoms of which zero to four are hereto ring atoms, said hetero ring atoms when present being selected from the group consisting of oxygen, sulphur and nitrogen, sulphur when present being optionally in the form of an —SO— or —SO$_2$— group, said phenyl ring being optionally further substituted by from one to three $R^2$ groups which are the same or different, said carbocyclic or heterocyclic ring being optionally substituted by one or more $R^{21}$ groups which are the same or different;

R is hydrogen or —CO$_2$R$^3$;

R$^1$ is:
  straight- or branched-chain alkyl having up to six carbon atoms, optionally substituted by one or more halogen; or
  cycloalkyl having from three to six carbon atoms, optionally bearing one or more substituents selected from the group consisting of $R^4$, —$CO_2R^4$, —$SR^4$, halogen and —$OR^4$;

$R^2$ is:
  halogen;
  straight- or branched-chain alkyl having up to six carbon atoms which is substituted by an —$OR^4$ group; or
  a member selected from the group consisting of $R^4$, —$CO_2R^4$, —$COR^4$, —$SR^5$, —$SO_2R^5$, —$OSO_2R^5$, —$OR^5$, —$O(CH_2)_m$—$OR^4$, —$NR^6R^7$, —$N(R^8)SO_2R^5$, —$(CR^9R^{10})_t$—$S(O)_pR^5$, nitro, cyano, and —$NR^{11}R^{12}$;

$R^{21}$ is as defined above for $R^2$ or represents =O, =S, cyclic ketal or cyclic thioketal;

each of $R^3$ and $R^4$, which are the same or different, is straight- or branched-chain alkyl, alkenyl or alkynyl having up to six carbon atoms, optionally substituted by one or more halogen;

$R^5$ is an $R^4$ group, or phenyl optionally bearing from one to five substituents which are the same or different selected from the group consisting of halogen, $R^4$, —$CO_2R^4$, —$COR^4$, —$OR^4$, nitro, cyano and —$O(CH_2)_m$—$OR^4$;

each of $R^6$ and $R^7$, which are the same or different, is hydrogen or straight- or branched-chain alkyl having up to six carbon atoms, optionally substituted by one or more halogen;

m is an integer from one to three;

$R^8$ is hydrogen; straight- or branched-chain alkyl, alkenyl or alkynyl having up to six carbon atoms, optionally substituted by one or more halogen; cycloalkyl having from three to six carbon atoms; or phenyl optionally substituted by from one to five $R^2$ groups which are the same or different;

each of $R^9$ and $R^{10}$, which are the same or different, is: hydrogen; straight- or branched-chain alkyl having up to 6 carbon atoms, optionally substituted by one or more halogen; or phenyl optionally bearing from one to five substituents which are the same or different selected from the group consisting of halogen, $R^4$, —$CO_2R^4$, —$COR^4$, —$OR^4$, nitro, cyano and —$O(CH_2)_m$—$OR^4$;

$R^{11}$ is —$COR^4$ or —$CO_2R^4$;

$R^{12}$ is:
  hydrogen;
  straight- or branched-chain alkyl having up to six carbon atoms, optionally substituted by one or more halogen; or
  cycloalkyl having from 3 to 6 carbon atoms;

p is zero, one or two; and t is an integer from one to three, provided that when t is greater than one, then the —$CR^9R^{10}$— groups are the same or different.

2. A compound of the formula

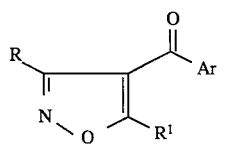

(I)

or an agriculturally acceptable salt thereof, wherein:

Ar is a phenyl ring having two substituents on adjacent positions which together with the two ring atoms to which they are attached form a saturated, partially saturated or aromatic carbocyclic or heterocyclic ring, said Ar being 1,3-benzodioxole, benzo[b]thiophene, benzoxazole or benzo-1,2,3-thiadiazole, each of which is optionally substituted by one or more $R^{21}$ groups which are the same or different;

R is hydrogen or —$CO_2R^3$;

$R^1$ is:
  straight- or branched-chain alkyl having up to six carbon atoms, optionally substituted by one or more halogen; or
  cycloalkyl having from three to six carbon atoms, optionally bearing one or more substituents selected from the group consisting of $R^4$, —$CO_2R^4$, —$SR^4$, halogen and —$OR^4$;

$R^2$ is:
  halogen;
  straight- or branched-chain alkyl having up to six carbon atoms which is substituted by an -$OR^4$ group; or
  a member selected from the group consisting of $R^4$, —$CO_2R^4$, —$COR^4$, —$SR^5$, —$SOR^5$, —$SO_2R^5$, —$OSO_2R^5$, —$OR^5$, —$O(CH_2)_m$— $OR^4$, —$NR^6R^7$, —$N(R^8)SO_2R^5$—$(CR^9R^{10})_t$—$S(O)_pR^5$, nitro, cyano, and —$NR^{11}R^{12}$;

$R^{21}$ is as defined above for $R^2$ or represents =O, =S, cyclic ketal or cyclic thioketal;

each of $R^3$ and $R^4$, which are the same or different, is straight- or branched-chain alkyl, alkenyl or alkynyl having up to six carbon atoms, optionally substituted by one or more halogen;

$R^5$ is an $R^4$ group, or phenyl optionally bearing from one to five substituents which are the same or different selected from the group consisting of halogen, $R^4$, —$CO_2R^4$, —$COR^4$, —$OR^4$, nitro, cyano and —$O(CH_2)_m$—$OR^4$;

each of $R^6$ and $R^7$, which are the same or different, is hydrogen or straight- or branched-chain alkyl having up to six carbon atoms, optionally substituted by one or more halogen;

m is an integer from one to three;

$R^8$ is hydrogen; straight- or branched-chain alkyl, alkenyl or alkynyl having up to six carbon atoms, optionally substituted by one or more halogen; cycloalkyl having from three to six carbon atoms; or phenyl optionally substituted by from one to five $R^2$ groups which are the same or different;

each of $R^9$ and $R^{10}$, which are the same or different, is: hydrogen; straight- or branched-chain alkyl having up to 6 carbon atoms, optionally substituted by one or more halogen; or phenyl optionally bearing from one to five substituents which are the same or different selected from the group consisting of halogen, $R^4$, —$CO_2R^4$, —$COR^4$, —$OR^4$, nitro, cyano and —$O(CH_2)_m$—$OR^4$;

$R^{11}$ is —$COR^4$ or $R^4$ or —$CO_2R^4$;

$R^{12}$ is:
  hydrogen;
  straight- or branched-chain alkyl having up to six carbon atoms, optionally substituted by one or more halogen; or
  cycloalkyl having from 3 to 6 carbon atoms;

p is zero, one or two; and t is an integer from one to three, provided that when t is greater than one, then the —$CR^9R^{10}$— groups are the same or different.

3. A compound of the formula

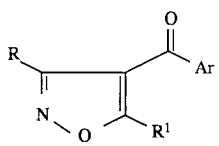

or an agriculturally acceptable salt thereof, wherein:

Ar is a phenyl ring having two substituents on adjacent positions which together with the two ring atoms to which they are attached form a saturated, partially saturated or aromatic carbocyclic or heterocyclic ring having five to seven ring atoms of which zero to four are hetero ring atoms, said hetero ring atoms when present being selected from the group consisting of oxygen, sulphur and nitrogen, sulphur when present being optionally in the form of an —SO— or —SO$_2$— group, said phenyl ring being optionally further substituted by from one to three R$^2$ groups which are the same or different, said carbocyclic or heterocyclic ring being optionally substituted by one or more R$^{21}$ groups which are the same or different; R is hydrogen or —CO$_2$R$^3$;

R$^1$ is:
straight- or branched-chain alkyl having up to six carbon atoms, optionally substituted by one or more halogen; or
cycloalkyl having from three to six carbon atoms, optionally bearing one or more substituents selected from the group consisting of R$^4$, —CO$_2$R$^4$, —SR$^4$, halogen and —OR$^4$;

R$^2$ is:
halogen;
straight- or branched-chain alkyl having up to six carbon atoms which is substituted by an —OR$^4$ group; or
a member selected from the group consisting of R$^4$, —CO$_2$R$^4$, —COR$^4$, —SR$^5$, —SOR$^5$, —SO$_2$R$^5$, —OSO$_2$R$^5$, —OR$^5$, —O(CH$_2$)$_m$—OR$^4$, —NR$^6$R$^7$, —N(R$^8$)SO$_2$R$^5$, —(CR$^9$R$^{10}$)$_t$-S(O)$_p$R$^5$, nitro, cyano, and —NR$^{11}$R$^{12}$;

R$^{21}$ is halogen, C$_2$-C$_4$ alkyl or —OR$_5$;

each of R$^3$ and R$^4$, which are the same or different, is straight- or branched-chain alkyl, alkenyl or alkynyl having up to six carbon atoms, optionally substituted by one or more halogen;

R$^5$ is an R$^4$ group, or phenyl optionally bearing from one to five substituents which are the same or different selected from the group consisting of halogen, R$^4$, —CO$_2$R$^4$, —COR$^4$, —OR$^4$, nitro, cyano and —O(CH$_2$)$_m$—OR$^4$;

each of R$^6$ and R$^7$, which are the same or different, is hydrogen or straight- or branched-chain alkyl having up to six carbon atoms, optionally substituted by one or more halogen;

m is an integer from one to three;

R$^8$ is hydrogen; straight- or branched-chain alkyl, alkenyl or alkynyl having up to six carbon atoms, optionally substituted by one or more halogen; cycloalkyl having from three to six carbon atoms; or phenyl optionally substituted by from one to five R$^2$ groups which are the same or different;

each of R$^9$ and R$^{10}$, which are the same or different, is:
hydrogen; straight- or branched-chain alkyl having up to 6 carbon atoms, optionally substituted by one or more halogen; or phenyl optionally bearing from one to five substituents which are the same or different selected from the group consisting of halogen, R$^4$, —CO$^2$R$^4$, —COR$^4$, —OR$^4$, nitro, cyano and —O(CH$_2$)$_m$—OR$^4$;

R$^{11}$ is —COR$^4$ or —CO$_2$R$^4$;

R$^{12}$ is:
hydrogen;
straight- or branched-chain alkyl having up to six carbon atoms, optionally substituted by one or more halogen; or
cycloalkyl having from 3 to 6 carbon atoms;

p is zero, one or two; and t is an integer from one to three, provided that when t is greater than one, then the —CR$^9$R$^{10}$— groups are the same or different.

4. A compound of the formula

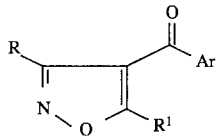

or an agriculturally acceptable salt thereof, wherein:

Ar is a phenyl ring having two substituents on adjacent positions which together with the two ring atoms to which they are attached form a saturated, partially saturated or aromatic carbocyclic or heterocyclic ring, said carbocyclic or heterocyclic ring being a five- or six-membered ring selected from the group consisting of dioxolane, thiophene, thiophene-S,S-dioxide, thiadiazole, oxazole, pyrrole and dioxane, said ring being optionally substituted by one or more R$^{21}$ groups which are the same or different;

R is hydrogen or —CO$_2$R$^3$;

R$^1$ is:
straight- or branched-chain alkyl having up to six carbon atoms, optionally substituted by one or more halogen; or
cycloalkyl having from three to six carbon atoms, optionally bearing one or more substituents selected from the group consisting of R$^4$, —CO$_2$R$^4$, —SR$^4$, halogen and —OR$^4$;

R$^2$ is:
halogen;
straight- or branched-chain alkyl having up to six carbon atoms which is substituted by an —OR$^4$ group; or
a member selected from the group consisting of R$^4$, —CO$_2$R$^4$, —COR$^4$, —SR$^5$, —SOR$^5$, —SO$_2$R$^5$, —OSO$_2$R$^5$, —OR$^5$, —O(CH$_2$)$_m$—OR$^4$, —NR$^6$R$^7$, —N(R$^8$)SO$_2$R$^5$, —(CR$^9$R$^{10}$)$_t$—S(O)$_p$R$^5$, nitro, cyano, and —NR$^{11}$R$^{12}$;

R$^{21}$ is as defined above for R$^2$ or represents =O, =S, cyclic ketal or cyclic thioketal;

each of R$^3$ and R$^4$ which are the same or different, is straight- or branched-chain alkyl, alkenyl or alkynyl having up to six carbon atoms, optionally substituted by one or more halogen;

R$^5$ is an R$^4$ group, or phenyl optionally bearing from one to five substituents which are the same or different selected from the group consisting of halogen, R$^4$, —CO$_2$R$^4$, —COR$^4$, —OR$^4$, nitro, cyano and —O(CH$_2$)$_m$— OR$^4$;

each of R$^6$ and R$^7$, which are the same or different, is hydrogen or straight- or branched-chain alkyl having up to six carbon atoms, optionally substituted by one or more halogen;

m is an integer from one to three;

$R^8$ is hydrogen; straight- or branched-chain alkyl, alkenyl or alkynyl having up to six carbon atoms, optionally substituted by one or more halogen; cycloalkyl having from three to six carbon atoms; or phenyl optionally substituted by from one to five $R^2$ groups which are the same or different;

each of $R^9$ and $R^{10}$, which are the same or different, is: hydrogen; straight- or branched-chain alkyl having up to 6 carbon atoms, optionally substituted by one or more halogen; or phenyl optionally bearing from one to five substituents which are the same or different selected from the group consisting of halogen, $R^4$, —$CO_2R^4$, —$COR^4$, —$OR^4$, nitro, cyano and —$O(CH_2)_m$—$OR^4$;

$R^{11}$ is —$COR^4$ or —$CO_2R^4$;

$R^{12}$ is:
hydrogen;
straight- or branched-chain alkyl having up to six carbon atoms, optionally substituted by one or more halogen; or
cycloalkyl having from 3 to 6 carbon atoms;

p is zero, one or two; and t is an integer from one to three, provided that when t is greater than one, then the —$CR^9R^{10}$— groups are the same or different.

5. A compound according to claim 1 wherein the carbocyclic or heterocyclic ring fused to the phenyl ring is a heterocyclic ring.

6. A compound according to claim 1 wherein:

(a) C-3 and C-4 of the phenyl ring are also ring atoms of the carbocyclic or heterocyclic ring, and C-2 of the phenyl ring bears an $R^2$ substituent; or (b) C-2 and C-3 of the phenyl ring are also ring atoms of the carbocyclic or heterocyclic ring, and C-4 of the phenyl ring bears an $R^2$ substituent.

7. A compound according to claim 2 wherein:

(a) C-3 and C-4 the phenyl ring are also ring atoms of the heterocyclic ring, and C-2 of the phenyl ring bears and $R^2$ substituent; or (b) C-2 and C-3 of the phenyl ring are also ring atoms of the heterocyclic ring, and C-4 of the phenyl ring bears an $R^2$ substituent.

8. A compound according to claim 1 wherein $R^2$ is halogen, —$SR^5$, —$SOR^5$, —$SO_2R^5$, $R^4$ or —$OR^5$.

9. A compound according to claim 2 wherein $R^2$ is halogen, —$SR^5$, —$SOR^5$, —$SO_2R^5$, $R^4$ or —$OR^5$.

10. A compound according to claim 6 wherein $R^2$ is halogen, —$SR^5$, —$SOR^5$, —$SO_2R^5$, $R^4$ or —$OR^5$.

11. A compound according to claim 2 wherein $R^{21}$ is halogen, $C_1$–$C_4$ alkyl or —$OR^5$.

12. A compound according to claim 6 wherein $R^{21}$ is halogen, $C_1$–$C_4$ alkyl or —$OR^5$.

13. A compound according to claim 8 wherein $R^{21}$ is halogen, $C_1$–$C_4$ alkyl or —$OR^5$.

14. A compound according to claim 3 wherein $R^{21}$ is fluoro, t-butyl or methoxy.

15. A compound according to claim 11 wherein $R^{21}$ is fluoro, t-butyl or methoxy.

16. A compound according to claim 12 wherein $R^{21}$ is fluoro, t-butyl or methoxy.

17. A compound according to claim 13 wherein $R^{21}$ is fluoro, t-butyl or methoxy.

18. A compound according to claim 1 wherein $R^1$ is straight- or branched-chain alkyl having tip to four carbon atoms, or cyclopropyl optionally substituted by an $R^4$ group.

19. A compound according to claim 2 wherein $R^1$ is straight- or branched-chain alkyl having up to four carbon atoms, or cyclopropyl optionally substituted by an $R^4$ group.

20. A compound according to claim 6 wherein $R^1$ is straight- or branched-chain alkyl having up to four carbon atoms, or cyclopropyl optionally substituted by an $R^4$ group.

21. A compound according to claim 8 wherein $R^1$ is straight- or branched-chain alkyl having up to four carbon atoms, or cyclopropyl optionally substituted by an $R^4$ group.

22. A compound according to claim 3 wherein $R^1$ is straight- or branched-chain alkyl having up to four carbon atoms, or cyclopropyl optionally substituted by an $R^4$ group.

23. A compound according to claim 18 wherein $R^1$ is cyclopropyl.

24. A compound according to claim 1 wherein R is hydrogen.

25. A compound according to claim 2 wherein R is hydrogen.

26. A compound according to claim 6 wherein R is hydrogen.

27. A compound according to claim 8 wherein R is hydrogen.

28. A compound according to claim 3 wherein R is hydrogen.

29. A compound according to claim 18 wherein R is hydrogen.

30. A compound according to claim 23 wherein R is hydrogen.

31. A compound according to claim 4 where $R^{21}$ is halogen, $C_1$–$C_4$ alkyl, —$SO_2R^5$ or —$OR^5$.

32. The compound according to claim 31 wherein R is hydrogen; $R^1$ is cyclopropyl; $R^2$ is halogen, —$SR^5$, —$SOR^5$, —$SO_2R^5$, —$CH_2S(O)_pR^5$, $R^4$ or —$OR^5$; $R^4$ is methyl; and $R^5$ is methyl or ethyl.

33. A compound according to claim 1 which is:

5-cyclopropyl-4-(2,2-difluoro-7-methylsulphenyl-1,3-benzodioxol-4-oyl)isoxazole;

5-cyclopropyl-4-(2,2-difluoro-1,3-benzodioxol-4-oyl) isoxazole;

5-cyclopropyl-4-(3,4-dimethoxybenzo[b]thien-5-oyl) isoxazole;

5-cyclopropyl-4-(benzo-1,2,3-thiadiazol-5-oyl)isoxazole;

5-cyclopropyl-4-(2,2-difluoro-7-methylsulphonyl-1,3-benzodioxol-4-oyl)isoxazole;

5-cyclopropyl-4-(2,2-difluoro-4-methylsulphonyl-1,3-benzodioxol-5-oyl)isoxazole;

4-(2-t-butyl-4-chlorobenzoxazol-7-oyl)-5-cyclopropylisoxazole;

4-(4-chloro-3-methoxybenzo[b]thien-5-oyl)-5-cyclopropylisoxazole;

5-cyclopropyl-4-(2,2-difluoro-4-methylsulphinyl-1,3-benzodioxol-5 -oyl)isoxazole;

5-cyclopropyl-4-(2,2-difluoro-4-methylsulphenyl-1,3-benzodioxol-5-oyl)isoxazole;

5-cyclopropyl-4-[1-(methylsulphonyl)indole-4-carbonyl] isoxazole;

5-cyclopropyl-4-(4-methyl-1,3-benzodioxol-5-oyl)isoxazole;

5-cyclopropyl-4-[4-(methanesulphonylmethyl)-1,3-benzodioxol-5-oyl]isoxazole;

5-cyclopropyl-4-[2,2-difluoro-4-(methanesulphonylmethyl)-1,3 -benzodioxol-5-oyl]isoxazole;

5-cyclopropyl-4-[4-(methylsulphenyl)-1,3-benzodioxol-5-oyl]isoxazole;

5-cyclopropyl-4-[3-ethoxy-4-(methylsulphenyl)benzo[b]thien-5-oyl]isoxazole;

5-cyclopropyl-4-(4-chloro-3-ethoxy-2-ethylbenzo[b]thien-5-oyl)isoxazole;

5-cyclopropyl-4-(4-chloro-3-ethoxybenzo[b]thien-5-oyl)isoxazole;

5-cyclopropyl-4-[2,3-dihydro-5-(methylsulphonyl)-1,3-benzodioxol-5-oyl]isoxazole;

5-cyclopropyl-4-[4-(methylsulphonyl)-1,3-benzodioxol-5-oyl]isoxazole;

5-cyclopropyl-4-[5-(methylsulphinyl)-1,4-benzodioxan-6-carbonyl]isoxazole;

5-cyclopropyl-4-[4-(methylsulphinyl)-1,3-benzodioxol-5-oyl]isoxazole;

5-cyclopropyl-4-(4-chloro-3-methoxybenzo[b]thien-5-oyl)isoxazole-1,1-dioxide;

5-cyclopropyl-4-(3,4-dimethoxybenzo[b]thien-5-oyl)isoxazole-1,1-dioxide;

5-cyclopropyl-4-(4-chloro-3-methoxy-2-methylbenzo[b]thien-5-oyl)isoxazole-1,1-dioxide;

5-cyclopropyl-4-[5-(methylsulphenyl)-1,4-benzodioxan-6-carbonyl]isoxazole; or 5-cyclopropyl-4-(4-chloro-3-methoxy-2-methylbenzo[b]thien-5-oyl)isoxazole.

34. A herbicidal composition comprising a herbicidally effective amount of a compound of formula (I) as defined in claim 1, or an agriculturally acceptable salt thereof, and at least one member of the group consisting of an agriculturally acceptable carrier and a surface active agent.

35. A herbicidal composition according to claim 34 in the form of an aqueous suspension concentrate, a wettable powder, a water soluble or water dispersible powder, a liquid water soluble concentrate, a liquid emulsifiable suspension concentrate, a granule or an emulsifiable concentrate.

36. A method for controlling the growth of weeds at a locus which comprises applying to the locus a herbicidally effective amount of a compound of formula (I) as defined in claim 1 or an agriculturally acceptable salt thereof.

* * * * *